US007566568B2

(12) United States Patent
Belardelli et al.

(10) Patent No.: US 7,566,568 B2
(45) Date of Patent: Jul. 28, 2009

(54) METHOD FOR GENERATING HIGHLY ACTIVE HUMAN DENDRITIC CELLS FROM PERIPHERAL BLOOD MONONUCLEAR CELLS

(75) Inventors: Filippo Belardelli, Rome (IT); Stefano Maria Santini, Rome (IT); Stefania Parlato, Rome (IT); Tiziana Di Pucchio, Isola del Liri (IT); Mariantonia Logozzi, Rome (IT); Caterina Lapenta, Florence (IT); Maria Ferrantini, Rome (IT); Laura Santodonato, Rome (IT); Giuseppina D'Agostino, Rome (IT)

(73) Assignee: Istituto Superiore di Sanita, Rome (IT)

( * ) Notice: Subject to any disclaimer, the term of this patent is extended or adjusted under 35 U.S.C. 154(b) by 956 days.

(21) Appl. No.: 09/845,042

(22) Filed: Apr. 27, 2001

(65) Prior Publication Data

US 2003/0092177 A1 May 15, 2003

(51) Int. Cl.
*C12N 5/00* (2006.01)
*C12N 5/02* (2006.01)

(52) U.S. Cl. ........................ 435/377; 435/384; 435/385

(58) Field of Classification Search ................. 435/325, 435/366, 377, 383
See application file for complete search history.

(56) References Cited

OTHER PUBLICATIONS

Paquette, R.L., et al. J. Leuk. Bio; Sep. 1998, 63:358-367.*
Bartholome, E.J., et al. J. Interferon and Cyt. Res.; May 1999, 19:471-478.*
Hart, D.N.J., "Dendritic Cells: Unique Leukocyte Populations Which Control the Primary Immune Response," *Blood,* vol. 90, No. 9, pp. 3245-3287 (1997).
Banchereau, J. and R.M. Steinman, "Dendritic cells and the control of immunity," *Nature*, vol. 392, pp. 245-252 (1998).
Bell, D., et al., "Dendritic Cells," *Adv. in Immunol.*, vol. 72, pp. 255-324 (1999).
Cella, M., et al., "Origin, maturation and antigen presenting function of dendritic cells," *Curr. Opin. Immunol.*, vol. 9, pp. 10-16 (1997).
Jonuleit, H., et al., "Induction of IL-15 Messenger RNA and Protein in Human Blood-Derived Dendritic Cells: A Role for IL-15 in Attraction of T Cells," *Journ. of Immunol.*, vol. 158, pp. 2610-2615.
Kuniyoshi, J.S., et al., "Dendritic Cell Secretion of IL-15 Is Induced by Recombinant huCD40LT and Augments the Stimulation of Antigen-Specific Cytolytic T Cells," *Cellular Immunology*, vol. 193, pp. 48-58 (1999).
Vella, A.T., et al., "Cytokine-induced survival of activated T cells in vitro and in vivo," *Proc Natl Acad Sci U.S.A.*, vol. 95, No. 7, pp. 3810-3815 (1998).
Borger, P., "Interleukin-15 differentially enhances the expression of interferon-γ and interleukin-4 in activated human (CD4+) T lymphocytes, " *Immunology*, vol. 96, pp. 207-214 (1999).
Avice, M., et al., "IL-15 Promotes IL-12 Production by Human Monocytes Via T Cell-Dependent Contact and May Contribute to IL-12-Mediated IFN-γ Secretion by CD4+ T Cells in the Absence of TCR Ligation," *Journ. of Immunol.*, vol. 161, pp. 3408-3415 (1998).
Sallusto, F., et al., " The Role of Chemokine Receptors in Primary, Effector, and Memory Immune Responses," *Annu. Rev. Immunol.*, vol. 18, pp. 593-620 (2000).
Dieu-Nosjean, M.C., et al., "Regulation of dendritic cell trafficking: a process that involves the participation of selective chemokines," *Journ. of Leukocyte Biology*, vol. 66, pp. 252-262 (1999).
Sozzani, S., et al., "Chemokines and Dendritic Cell-Traffic," *Journ. of Clinical Immunol.*, vol. 20, No. 3, pp. 151-160 (2000).
Schall, T.J. and K.B. Bacon, "Chemokines, leukocyte trafficking, and inflammation," *Curr. Opin. in Immunol.*, vol. 6, pp. 865-873 (1994).
Sozzani, S., et al., "Migration of Dendritic Cells in Response to Formyl Peptides, C5a, and a Distinct Set of Chemokines," *Journ. of Immunol.*, vol. 155, pp. 3292-3295 (1995).
Sozzani, S., "Differential Regulation of Chemokine Receptors During Dendritic Cell Maturation: A Model for Their Trafficking Properties," *Journ. of Immunol.*, vol. 161, pp. 1083-1086 (1998).
Qin, S., et al., "The Chemokine Receptors CXCR3 and CCR5 Mark Subsets of T Cells Associated with Certain Inflammatory Reactions," *J. Clin. Invest.*, vol. 101, No. 4, pp. 746-754 (1998).
Liu, M.T., et al., "The T Cell Chemoattractant IFN-Inducible Protein 10 Is Essential in Host Defense Against Viral-Induced Neurologic Disease," *Journ. of Immunol.*, vol. 165, pp. 2328-2330 (2000).
Andrew, D. P., et al., "STCP-1 (MDC) CC Chemokine Acts Specifically on Chronically Activated Th2 Lymphocytes and Is Produced by Monocytes on Stimulation with Th2 Cytokines IL-4 and IL-13," *Journ. of Immunol.*, vol. 161, pp. 5027-5038 (1998).
Sallusto, F. and A. Lanzavecchia, "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med.*, vol. 179, pp. 1109-1118 (1994).
Romani, N., et al., "Proliferating Dendritic Cell Progenitors in Human Blood," *J. Exp. Med.*, vol. 180, pp. 83-93 (1994).
Caux, C., et al., "GM-CSF and TNF-α cooperate in the generation of dendritic Langerhans cells," *Nature*, vol. 360, pp. 258-261 (1992) .
Reddy, A., et al., "A Monocyte Conditioned Medium Is More Effective Than Defined Cytokines in Mediating the Terminal Maturation of Human Dendritic Cells," *Blood*, vol. 90, No. 9, pp. 3640-3646 (1997).
Goxe, B., et al., "Monocyte-derived dendritic cells: development of a cellular processor for clinical applications," *Res. Immunol.*, vol. 149, pp. 643-646 (1998).

(Continued)

*Primary Examiner*—G. R Ewoldt
(74) *Attorney, Agent, or Firm*—Young & Thompson

(57) ABSTRACT

The present invention relates to a process for deriving dendritic cells from mononuclear cells in culture comprising the step of putting in contact type I IFN with said mononuclear cells. Dendritic cells suitable as cellular adjuvants in prophylactic as well as therapeutic vaccination of animal and human beings, are obtainable thereby, after a single step treatment in a brief period of time. Dendritic cells obtainable thereby, pharmaceutical compositions including them, in particular a vaccine comprising said cells as active principle, and a method of treatment of a pathology associated with the presence of an antigen in human beings, are further objects of the invention, as well as a kit for deriving said dendritic cells and a method for the ex vivo expansion of T cells using them.

22 Claims, 11 Drawing Sheets

OTHER PUBLICATIONS

Santini, S.M., et al., "Type I Interferon as a Powerful Adjuvant for Monocyte-derived Dendritic Cell Development and Activity In Vitro and in Hu-PBL-SCID Mice," *J. Exp. Med.*, vol. 191, No. 10, pp. 1777-1788 (2000).

Forster, R., et al ., "CCR7 Coordinates the Primary Immune Response by Establishing Functional Microenvironments in Secondary Lymphoid Organs," *Cell*, vol. 99, pp. 23-33 (1999).

Rossio, J. L., et al., "Inactivation of Human Immunodeficiency Virus Type 1 Infectivity with Preservation of Conformational and Functional Integrity of Virion Surface Proteins," *Journ. of Virology*, vol. 72, No. 10, pp. 7792-8001 (1998).

Mosier, D. E., et al., "Transfer of a functional human immune system to mice with severe combined immunodeficiency," *Nature*, vol. 335, pp. 256-259 (1988).

Coccia, M. A., et al., "Higher Titer, Prostate Specific Antigen-Specific Human IgG. Production by hu-PBL-SCID Mice Immunized with Antigen-Mouse IgG2a Complex-Pulsed Autologous Dendritic Cells," *Journ. of Immunol.*, vol. 161, pp. 5772-5780 (1998).

Mosier, D. E., et al., "Studies of HIV Infection and the Development of Epstein-Barr Virus-Related B Cell Lymphomas Following Transfer of Human Lymphocytes to Mice With Severe Combined Immunodeficiency," *Current Topics in Microbiology and Immunology*, vol. 152, pp. 195-199 (1989).

Rowe, M., et al., "Epstein-Barr Virus (EBV)-associated Lymphoproliferative Disease in the SCID Mouse Model: Implications for the Pathogenesis of EBV-positive Lymphomas in Man," *J. Exp. Med.,* vol. 173, pp. 147-158 (1991).

* cited by examiner

A
³H-Thymidine incorporation (cpm)
40000
30000
20000
10000
0
IL-4/GM-CSF
IFNα2a/GM-CSF
IFNαn/GM-CSF
IFNβ/GM-CSF
B
IFNγ Elispot assay
IFNβ/GM-CSF
IFNαn/GM-CSF
CIFN/GM-CSF
IL-4/GM-CSF
0
50
100
150
200
250
300
Spot forming cells/10⁸
C
IFNγ pg/ml
5000
4000
3000
2000
1000
0
IL-4 pg/ml
800
600
400
200
0
IL-4/GM-CSF
CIFN/GM-CSF
IFNαn/GM-CSF
IFNβ/GM-CSF

SEQUENCE LISTING

```
<160> NUMBER OF SEQ ID NOS: 37

<210> SEQ ID NO 1
<211> LENGTH: 30
<212> TYPE: DNA
```

-continued

```
<213> ORGANISM: Artificial Sequence
<220> FEATURE:
<223> OTHER INFORMATION: Description of Artificial Sequence: Primer

<400> SEQUENCE: 1

cttcatcttt gaagaagaac ctatcttctt                                     30


<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2

aatttttggg atctacactc tccagctgta                                     30


<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3

atgagcactg aaagcatgat ccgg                                           24


<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 4

gcaatgatcc caaagtagac ctgccc                                         26


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 5

ccaagaactt gcagctgaag a                                              21


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6

tgggtctatt ccgttgtgtc                                                20


<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 7

ctcgtctaga gccaactggg tgaatgtaat aag                                 33
```

-continued

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 8
tacttactcg aggaatcaat tgcaatcaag aagtg 35

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
tctgactgta gagataatgc 20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
gaacagtgaa cattatagat c 21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
tccttctcat cagcaagctg tc 22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
gaggcagccc aggtccttga ag 22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 13
caccctccat ggccctgcta ct 22

<210> SEQ ID NO 14
<211> LENGTH: 22
<212> TYPE: DNA
<213> ORGANISM: Artificial Sequence
<220> FEATURE:

-continued

<223> OTHER INFORMATION: Description of Artificial Sequence: Primer

<400> SEQUENCE: 14
taactgctgc ggcgcttcat ct 22

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
acaaagagct ctgctgcctc 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
cccacttctt attggggtca 20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 17
cctcctcctg ggggcttctc tg 22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
gactttaatc tgggcccttt gtgc 24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 19
tgatttgctg ccttatcttt ctga 24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 20
cagcctctgt gtggtccatc cttg 24

-continued

```
<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21

cagcctgaca aatcacagtg                                                  20


<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 22

ctggatgaca ctgagctgg                                                   19


<210> SEQ ID NO 23
<211> LENGTH: 21
<212> TYPE: PRT
<213> ORGANISM: Human Immunodeficiency Virus type 1

<400> SEQUENCE: 23

Glu Arg Tyr Leu Lys Asp Gln Gln Leu Leu Gly Ile Trp Gly Cys Ser
  1               5                  10                  15

Gly Lys Leu Ile Cys
             20


<210> SEQ ID NO 24
<211> LENGTH: 9
<212> TYPE: PRT
<213> ORGANISM: Epstein-Barr Virus

<400> SEQUENCE: 24

Cys Leu Gly Gly Leu Leu Thr Met Val
  1               5


<210> SEQ ID NO 25
<211> LENGTH: 10
<212> TYPE: PRT
<213> ORGANISM: Epstein-Barr Virus

<400> SEQUENCE: 25

Leu Leu Asp Phe Val Arg Phe Met Gly Val
  1               5                  10


<210> SEQ ID NO 26
<211> LENGTH: 9
<212> TYPE: PRT
<213> ORGANISM: Epstein-Barr Virus

<400> SEQUENCE: 26

Gly Leu Cys Thr Leu Val Ala Met Leu
  1               5


<210> SEQ ID NO 27
<211> LENGTH: 9
<212> TYPE: PRT
<213> ORGANISM: Epstein-Barr Virus

<400> SEQUENCE: 27

Leu Leu Trp Thr Leu Val Val Leu Leu
```

-continued 1 5

<210> SEQ ID NO 28
<211> LENGTH: 9
<212> TYPE: PRT
<213> ORGANISM: Epstein-Barr Virus

<400> SEQUENCE: 28

Ser Val Arg Asp Arg Leu Ala Arg Leu
1 5

<210> SEQ ID NO 29
<211> LENGTH: 9
<212> TYPE: PRT
<213> ORGANISM: Epstein-Barr Virus

<400> SEQUENCE: 29

Val Leu Gln Trp Ala Ser Leu Ala Val
1 5

<210> SEQ ID NO 30
<211> LENGTH: 9
<212> TYPE: PRT
<213> ORGANISM: Epstein-Barr Virus

<400> SEQUENCE: 30

Gly Ile Leu Gly Phe Val Phe Thr Leu
1 5

<210> SEQ ID NO 31
<211> LENGTH: 8
<212> TYPE: PRT
<213> ORGANISM: Epstein-Barr Virus

<400> SEQUENCE: 31

Arg Leu Arg Ala Glu Gln Val Lys
1 5

<210> SEQ ID NO 32
<211> LENGTH: 9
<212> TYPE: PRT
<213> ORGANISM: Epstein-Barr Virus

<400> SEQUENCE: 32

Tyr Pro Leu His Glu Gln His Gly Met
1 5

<210> SEQ ID NO 33
<211> LENGTH: 9
<212> TYPE: PRT
<213> ORGANISM: Epstein-Barr Virus

<400> SEQUENCE: 33

Ala Val Leu Leu His Glu Glu Ser Met
1 5

<210> SEQ ID NO 34
<211> LENGTH: 9
<212> TYPE: PRT
<213> ORGANISM: Epstein-Barr Virus

<400> SEQUENCE: 34

Gln Pro Arg Ala Pro Ile Arg Pro Ile
1 5

-continued

```
<210> SEQ ID NO 35
<211> LENGTH: 9
<212> TYPE: PRT
<213> ORGANISM: Epstein-Barr Virus

<400> SEQUENCE: 35

Ile Val Thr Asp Phe Ser Val Ile Lys
  1               5


<210> SEQ ID NO 36
<211> LENGTH: 9
<212> TYPE: PRT
<213> ORGANISM: Epstein-Barr Virus

<400> SEQUENCE: 36

Arg Pro Pro Ile Phe Ile Arg Arg Leu
  1               5


<210> SEQ ID NO 37
<211> LENGTH: 10
<212> TYPE: PRT
<213> ORGANISM: Epstein-Barr Virus

<400> SEQUENCE: 37

Ala Val Phe Asp Arg Lys Ser Asp Ala Lys
  1               5                  10
```

METHOD FOR GENERATING HIGHLY ACTIVE HUMAN DENDRITIC CELLS FROM PERIPHERAL BLOOD MONONUCLEAR CELLS

FIELD OF THE INVENTION

The present invention relates to the field of immunotherapy, and in particular to vaccines including as an adjuvant human or animal dendritic cells.

BACKGROUND OF THE INVENTION

Dendritic cells (DCs) are known in the art. In absence of lineage specific markers, they are generally identified by the lack of leukocyte markers of other lineages (CD3 for T cell lineage, CD14 and CD15 for monocytic and granulocyte lineages, CD19, CD20 and CD24 for B cell lineage and CD16, CD56 and CD57 for NK cell lineage) by their specific immunophenotype (positive for surface antigen CD40, CD80, CD86), and their morphology (characterized by the presence of dendrites or membrane processes) (1-3).

From the functional point of view, DCs are known to be highly potent antigen-presenting cells (APC), playing in vivo a pivotal role in the priming of the immune response (1-3). In this connection, a main distinction is made between mature and immature DCs.

Immature DCs are weak initiators of immune response specialized in capturing and processing antigens, phenotypically characterized by low expression of the accessory molecules CD40, CD80, CD86 and the lack of CD83 expression. Upon appropriate stimuli, DCs undergo extensive changes: loss of antigen-capturing function and the upregulation of the expression of costimulatory molecules (CD40, CD80 and CD86) together with the induction of CD83 and CD25 (1-4).

Terminally differentiated/mature DCs are instead capable of readily priming naive T cells within lymphoid tissues.

Phenotype of DCs in the mature state is characterized accordingly by the production of a variety of cytokines, including typically IL-15, (1-3, 5, 6) which are considered capable to affect, by autocrine/paracrine mechanisms, the phenotype and functional activity of DCs themselves as well as of other host cells (7-9).

Phenotype of mature/activated DCs is also characterized by specific chemotactic properties. In this connection, it is well known in the art that migration of DCs is tightly regulated as a function of maturation (10-13).

Thus, immature DCs respond to inflammatory chemokines, such as MIP-1$\alpha$, MIP-1$\beta$, RANTES and MIP-3$\alpha$ (14) as a consequence of the expression of the chemokine receptors CCR5 and CCR6, while mature DCs have lost their responsiveness to most of these chemokines, as a result of downregulation of cognate receptor expression or activity (15).

Conversely, mature DCs have been reported to respond to MIP-3$\beta$/ELC and 6Ckine/SLC as a consequence of the induction of their specific receptor CCR7 which is lacking on immature DCs (10, 11, 15).

On the other hand, DCs are themselves producer of a series of chemokines. Upon maturation, DCs have an initial burst of Mip-3$\alpha$, Mip-3$\beta$ and IL-8, whereas RANTES and MCP-1 are produced in a more sustained fashion. The production of MIP-3$\beta$/ELC by activated/mature DCs is also important in supporting the generation of the immune response by recruiting naive T and B cells, which selectively express CCR7.

Mature DCs express also IP-10, a potent chemoattractant for activated/memory Th1 cells by binding to the receptor CXCR3 (10, 16, 17), while immature DCs express MDC and TARC attracting specifically chronically activated Th2 lymphocytes. (10, 18). In addition, in presence of mature DCs and IL-12, T-helper cells turn into IFN$\gamma$-producing Th1 cells, which promote the cellular arm of the immune response, whereas $CD8^+$ cytotoxic T cells are induced to proliferate vigorously. IFN$\gamma$ and IL-12 promote further the differentiation of T cells into killer cells.

Accordingly, mature DCs are considered capable of stimulating the outgrowth and activation of a variety of T cells.

The ability to prime antigen-specific naive T cells represent a unique and critical function of DCs. Moreover, by virtue of their enhanced expression of HLA and costimulatory molecules, DCs stimulate allogeneic MLR (which allows comparison of the capacity of different APCs to stimulate T cell proliferation independently of the antigen) more efficiently than any other antigen presenting cell. Thus, there is a growing interest in utilizing such cells as cellular adjuvants for prophylactic or therapeutic vaccination toward infectious agents or tumors.

However, the use of DCs has been limited by their very low frequency in peripheral blood and the invasiveness of procedures aimed to gain access to bone marrow or lymphoid organs. Such limitations render complicate and expensive obtaining DCs to be used as adjuvant and application related thereto.

Consequently, some processes allowing production of DCs in vitro have been defined. These procedures are all based on the information that DCs originate from progenitor $CD34^+$ cells in bone marrow and blood or can be derived from peripheral blood mononuclear $CD14^+$ cells (19, 20). Hence, according to a first approach DCs are generated by cultivation of $CD34^+$ progenitors in medium containing Flt3-L or SCF (stem cell factor), followed by a combinations of various cytokines including GM-CSF, IL-4, and TNF$\alpha$ (3, 4).

In a second approach, an initial phase of cultivation of progenitors $CD34^+$ cells is carried out in the presence of GM-CSF, TNF-$\alpha$ and IL-4 (PCT/AU97/00801) followed by treatment with type I IFN.

Following a further approach, $CD34^+$ precursor cells from cord blood or bone marrow are cultivated in presence of IL-3 or GM-CSF (21). Thus, this procedure has been shown to induce cell proliferation, which is strongly potentiated by TNF$\alpha$ and culminates in the appearance of $CD1a^+$ cells displaying typical DC morphology and surface markers. $CD34^+$ precursor cells cultured in the presence of GM-CSF and TNF$\alpha$ differentiate into two distinct DC populations within 5-7 days, as defined by the exclusive expression of CD14 and CD1a. However, by further culturing, CD1a expression is generally downregulated just as CD83 appears (3).

According to a fourth approach, immature DCs are generated starting from peripheral blood $CD14^+$ monocytes cultivated in GM-CSF in conjunction with IL-13 or IL-4 for 5-7 days. DCs produced according to this procedure, however, display features of and behave as immature DCs expressing low levels of CD80 and CD86. Consequently, these DCs act as weak stimulators of a specific T cell response and MLR. In this setting, further DC maturation can be driven by the addition of TNF$\alpha$, IL-1, LPS, monocyte-conditioned medium (22) or sCD40L for two additional days (2, 3).

Thus, the requirement of a further step for DC maturation by addition of other factors to immature DCs represents a strong limitation for the rapid generation of DCs highly effective for clinical purposes. Moreover, it is not clear whether the use of mature DCs represents an advantage over immature DCs for clinical applications. In this context, DCs endowed with intermediate phenotypic and functional properties, i.e.: high phagocytic activity associated to the expression of membrane markers typical of mature DCs and to a potent immunostimulatory capacity, would represent a novel cellular entity of great interest for clinical applications.

SUMMARY OF THE INVENTION

Object of the present invention is to provide a process which allows a rapid generation of partially mature and highly functional DCs, suitable as cellular adjuvants in prophylactic as well as therapeutic vaccination of animal and human beings.

Such an object is achieved according to a first aspect of the present invention by a process for deriving dendritic cells from mononuclear cells in culture, comprising the step of putting in contact said mononuclear cells with type I interferon at a final concentration greater than 100 IU/ml, since the initial culture thereof.

A first advantage of the process of the invention is given in that partially mature DCs are obtainable thereby from freshly isolated monocytes after a single step treatment including type I IFN as an essential factor.

A second advantage of the process of the invention is that it provides a particularly rapid procedure for DC production which can be carried out in a brief period of time (within three days of culture).

A third and main advantage is the generation of highly stable and partially mature DCs. Such DCs are endowed with more powerful "in vitro" and "in vivo" activities than those exhibited by DCs obtainable by the procedure known in the art.

In this connection the process of the invention is preferably carried out within three days of culture and more preferably, in presence of a growth factor, such as GM-CSF (Granulocyte/Monocyte-Colony Stimulating Factor) or the like, which promotes monocyte/DC survival in culture.

The GM-CSF is used preferably at a concentration in a range of 250-1,000 U/ml.

Type I IFN suitable in the process of the invention can be selected from the group consisting of any natural IFNα, any recombinant species or subtype of IFNα, consensus IFN (IFNcon1, herein named also CIFN), natural or recombinant IFNβ, and any synthetic type I IFN.

As reported above, IFN shall generally be present in the culture medium at a final concentration greater than 100 IU/ml. Preferred embodiments in this connection are, however the ones wherein type I IFN is present in a concentration comprised in a range of 100-10,000 IU/ml, or more preferably in a range of 400-10,000 IU/ml, or 500-2,000 IU/ml, particularly 1,000 IU/ml. Using the latter range and concentration, DCs acquire the optimal expression of membrane markers associated with functional activity, with minimal toxic effects and good cell viability.

Since the GM-CSF is a constant culture component for monocyte-derived DCs, effects of differentiation are ascribed to IFN for DC populations originated in presence of IFN/GM-CSF (herein also defined IFN-DCs).

Mononuclear cells particularly preferred in the process of the invention are the one previously isolated from peripheral blood mononuclear cells (PBMC), and particularly $CD14^+$ monocytes, in an embodiment which has the further advantage of employing an easily available starting product. Alternatively, total unseparated or adherent PBMC are utilized in the procedure described.

The cells can be cultured in any medium suitable for culturing DCs "in vitro". In the specific case of treatment of human patients, culture media like X-VIVO 20 or AIM-V, are preferably used.

In a further preferred embodiment the process of the invention comprises also the step of putting in contact the cells treated with type I IFN with a maturation agent. Such an embodiment can be particularly suitable in all the cases, which can be identified by a skilled person, wherein a further maturation of the DCs obtained by treating the mononuclear cells with type I IFN as reported above is desired.

As reported above, a main advantage of the process of the invention is that it allows the production of DCs which are highly stable and functional.

Such DCs, as described in details below, exhibit in fact an immunophenotype, morphology, chemotaxis, and immunological activity not present in DCs derived according to other processes known in the art. Such features render DCs of the invention particularly suitable as an adjuvant in vaccine administration.

In particular, DCs obtainable by the process of the invention (IFN-DCs) are better stimulators of T and B cell response as compared to DCs differentiated in the presence of GM-CSF and IL-4 (IL-4-DCs), and induce a pronounced polarization of immune response toward the Th1 type.

DCs obtainable by the process of the invention, which in a preferred embodiment are loaded with antigenic peptides or proteins, or with a cellular extract containing at least one antigen, or with nucleic acids, are accordingly a further object of the present invention, as well as vaccines including DCs of the invention as an adjuvant or as an active principle, together with an antigen and a pharmaceutical acceptable carrier vehicle or auxiliary agent, and a process for producing said vaccine comprising the step of including in said vaccine as an adjuvant the DCs of the invention.

Any vehicle, carrier, auxiliary agent and formulation adopted in art for manufacturing vaccines can be used in the vaccine of the invention. A skilled person can identify said components and all the steps of the relevant process of manufacturing.

Due to the adjuvant activity of the DCs of the invention, a further object of the present invention is a method for prophylaxis and/or therapy of pathologies associated with the presence of an antigen in the human body comprising the step of administering a vaccine including an immunogen for said antigen and DCs of the invention as an adjuvant to a subject in need thereof.

Such an antigen, including viral, bacterial and tumor antigens, can be any molecule the presence of which is associated with a pathology.

The DCs of the invention can be injected without prior incubation with specific antigens into a subject in need thereof, so that antigens are locally acquired by DCs.

In this connection, due to their properties, the DCs of the invention can be used also as an active principle in a pharmaceutical composition comprising the DCs of the invention together with a pharmaceutically acceptable carrier, vehicle or auxiliary agent, said carrier vehicle and auxiliary agent being identifiable by a person skilled in the art.

Said pharmaceutical composition is suitable according to the invention in a method for the treatment of a pathology associated with the presence of an antigen in the human body, which comprises the step of administering said pharmaceutical composition to a subject in need thereof. The pathology treatable with said method can be an infection or a neoplastic disease, and the administration can be preferentially located at the site of the infection or within the primary tumor, metastases or draining lymph nodes.

The DCs of the invention can also be used for the ex vivo expansion of T cells, which can be CD4+ and/or CD8+ or both, in a method for the ex vivo expansion of T cells comprising the step of putting in contact said T cells with the dendritic cells of the invention. T cells so treated can be administered to humans for treating immune disorders or deterioration.

Object of the present invention is also a kit containing means for the preparation of DCs. This kit contains means for the reduction to practice of the process described in the present application. Those means may include: possible means for the recovery of mononuclear cells from PBMC; appropriate buffer, wash and cells conservation solutions; means for preparing a culture medium for the mononuclear cells, and complements for the culture medium, such as type I IFN and possibly GM-CSF.

Accordingly, a further object of the invention is given by a kit for deriving DCs from mononuclear cells in culture, comprising a composition comprising type I IFN and compatible additives, a composition comprising a cell growth factor and compatible additives, and a culture medium, for simultaneous separate or sequential use in the process of the invention.

A skilled person can easily identify the additives suitable in the compositions reported above, among the chemically compatible additives known in the art.

A better description of the invention will be given with the help of the annexed figures.

Panel B shows secretion of IL-15 in DC culture supernatant. Histograms represent the concentration of IL-15 protein, as assessed by ELISA, in supernatants from DCs generated in the presence of 1,000 IU/ml of different type I IFN preparations and in the presence of 500 U/ml of IL-4, in all cases in conjunction with 500 U/ml of GM-CSF for 3 days. Values are expressed as mean of 3 experiments ±S.D.

Figure 6:
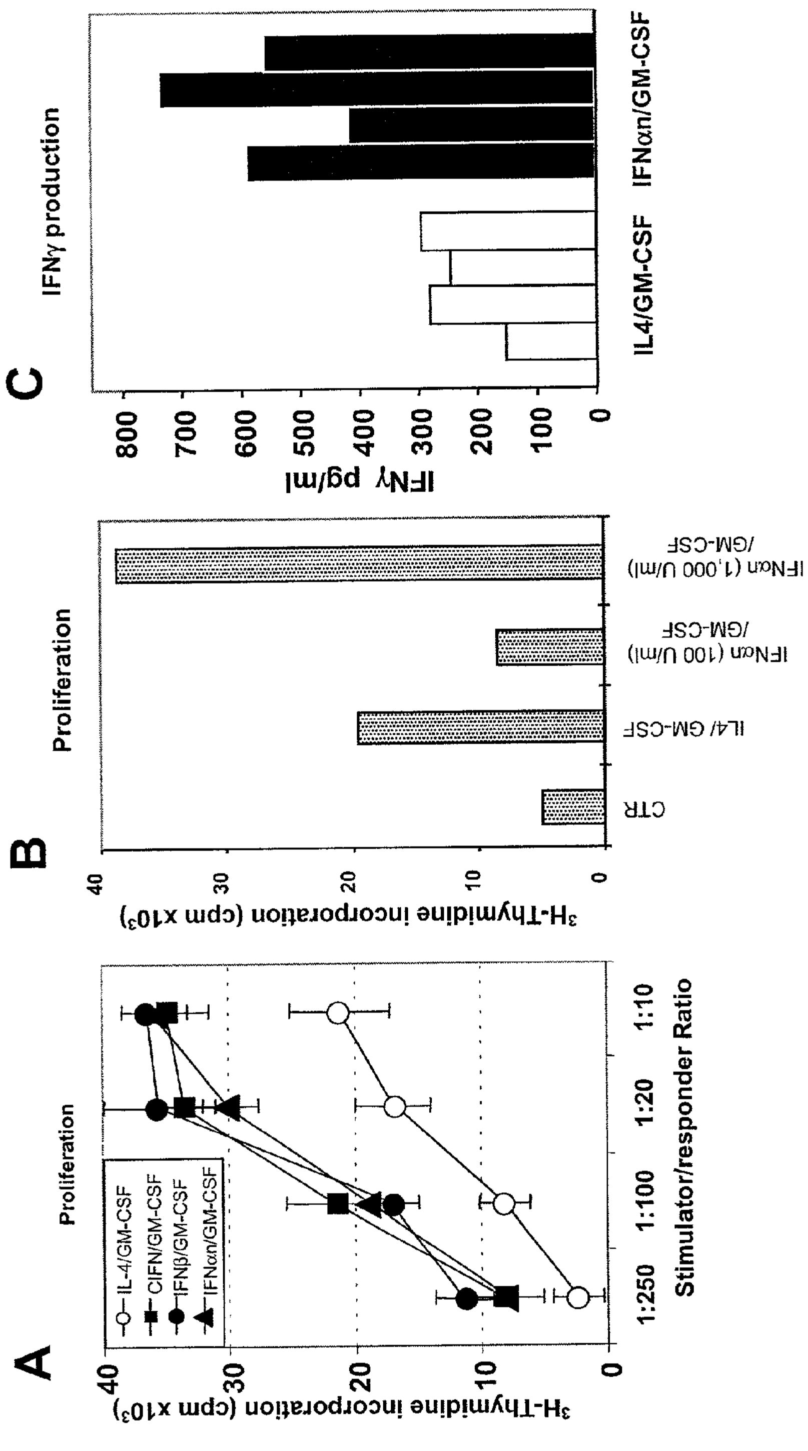

FIG. 6, panel A shows a comparative MLR assay with DCs generated in the presence of various preparations of type I IFN and GM-CSF or IL-4/GM-CSF. Allogeneic PBLs were stimulated by DCs (at different stimulator/responder ratio) previously cultured for 3 days with IFN/GM-CSF or IL-4/GM-CSF. Lymphocyte proliferation was evaluated by $^3$H-Thymidine incorporation, measured by β-radiation scintillation counting as described in the examples.

Panel B shows the effect of 100 and 1,000 IU/ml of IFN in combination with 500 U/ml of GM-CSF on the ability of DCs to induce proliferation of allogeneic lymphocytes at a stimulator to responder ratio of 1:20 (allogeneic MLR). Histograms represent $^3$H-Thymidine incorporation evaluated by β-radiation scintillation counting.

Panel C shows IFNγ production in the supernatants from allogeneic MLRs after 5 days of co-culture. PBLs from each of four different donors were stimulated at a stimulator: responder ratio of 1:20, with allogeneic DCs generated by culturing the cells in the presence of either IFNαn/GM-CSF or IL-4/GM-CSF for 3 days. Each bar represents IFNγ concentration in the supernatant from MLR cultures of DCs with PBLs from individual allogeneic donors, as evaluated by commercial ELISA kit.

Figure 7:
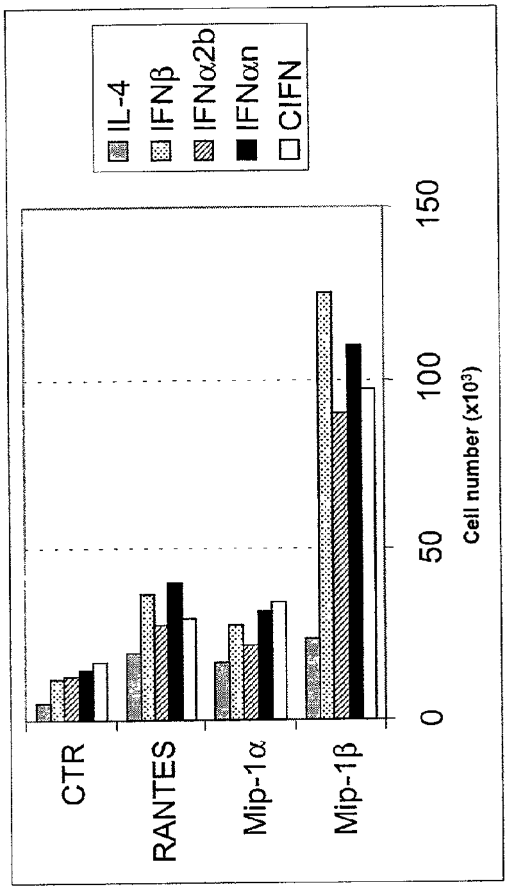

FIG. 7 shows the comparative analysis of DC chemotactic response to β-chemokines. DCs were generated with different preparations of type I IFN or IL-4 in the presence of GM-CSF. $5\times10^5$ DCs, generated after 3 days of treatment with GM-CSF and the indicated cytokine were resuspended in complete medium and seeded in the upper compartments of 8 μm-pore size filter transwell chambers, while 0.5 μg/ml of the relevant chemokine in serum-free medium were added to the lower compartments. The lower wells of control chambers contained medium alone. Bars represent the number of cells migrated to the lower compartment, in response to chemokines, after a 2 hr incubation. Assays were performed in triplicate.

Figure 8:
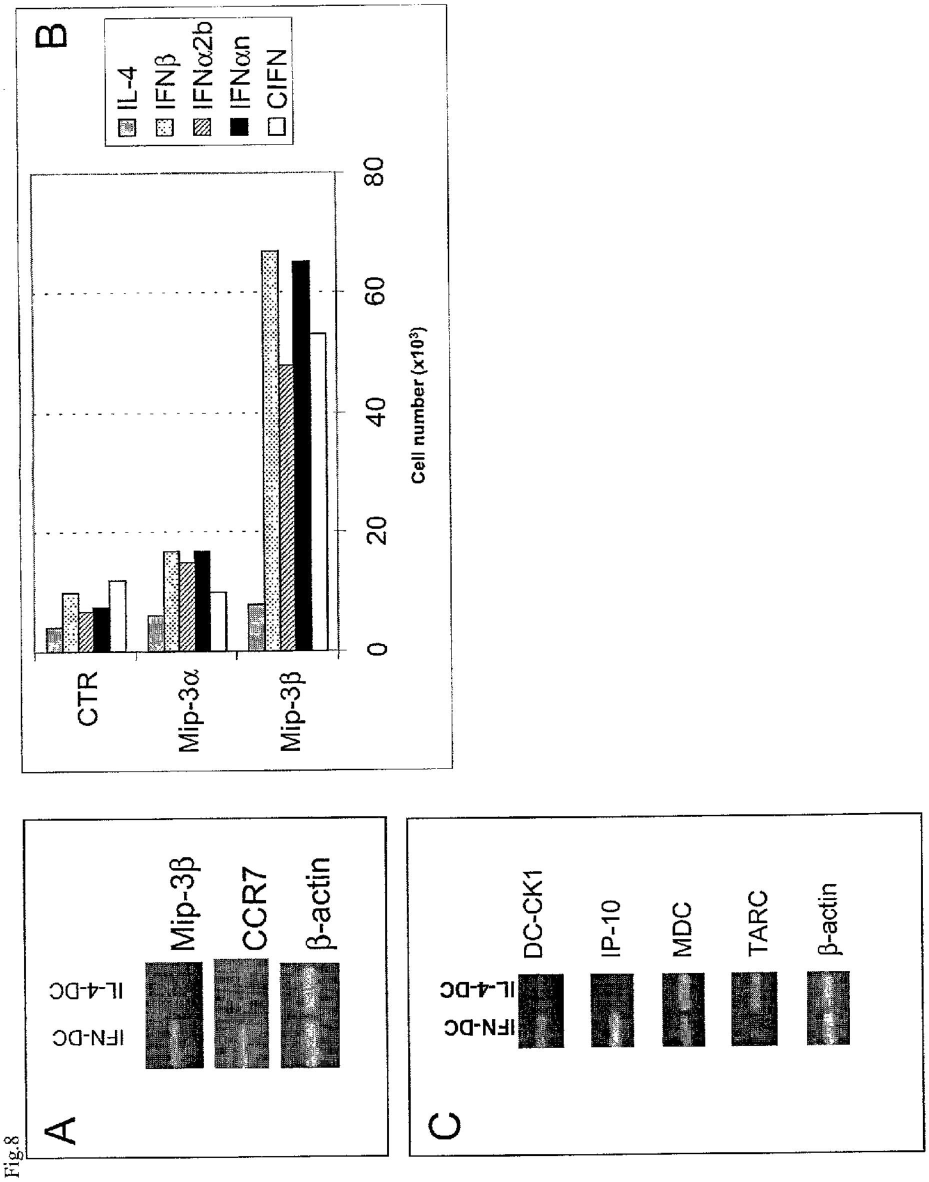

FIG. 8, panel A, shows the expression at mRNA level of the chemokine MIP-3β and its receptor CCR7 in IFN-DCs as compared to IL-4-DCs. PCR products were photographed upon transillumination of 1.5% agarose electrophoresis gels stained with ethidium bromide. Panel B shows the migratory response of IL-4-DCs vs. IFN-DCs, generated with GM-CSF and different IFN preparations as indicated, elicited by MIP-3α and MIP-3β. Chemotactic assays were performed as described for FIG. 7. Bars represent the number of cells migrated to the lower compartment, in response to chemokines, after a 2 hr incubation. Assays were performed in triplicate.

Panel C shows chemokine expression in IFN-DCs vs. IL-4-DCs as evaluated by RT-PCR analysis performed after 3 days of treatment of monocytes with either IFN/GM-CSF or IL4/GM-CSF. PCR products were photographed upon transillumination of 1.5% agarose electrophoresis gels stained with ethidium bromide.

Figure 9:
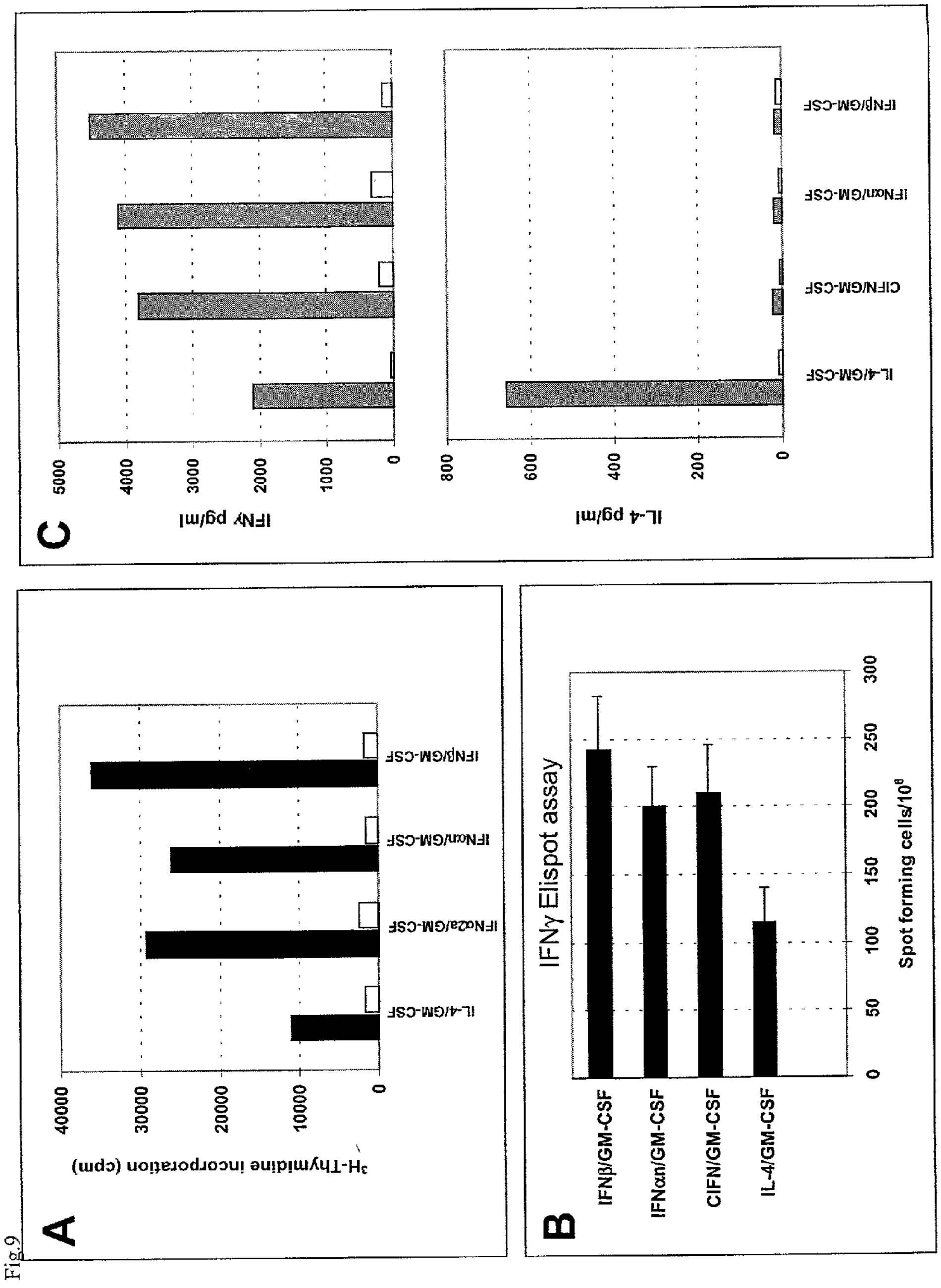

FIG. 9 shows the “in vitro” induction of primary immune response to HIV-1 antigens in PBLs cocultivated with autologous DCs pulsed with inactivated HIV-1.

DCs were generated by treatment of freshly isolated monocytes with different type I IFN preparations and GM-CSF or IL-4/GM-CSF for 3 days as described in the Examples. PBLs were stimulated on day 0 and restimulated on day 7 with the autologous DCs pulsed with AT-2-inactivated HIV-1 at a stimulator:responder ratio of 1:4. Control cultures were incubated with unpulsed autologous DCs. Exogenous IL-2 (25 U/ml) was added every 4 days. At day 14, the cultures were re-stimulated with DCs pulsed with AT-2 inactivated HIV-1 and, after 24 hr, $^3$H-thymidine was added. Cells were harvested after a 18 hr incubation. Cells and supernatants from the cell cultures were tested for IFNγ production by ELISPOT analysis (panel B) and ELISA (panel C).

Panel A shows the results of lymphocyte proliferation assays to HIV antigens using DCs as APCs, as evaluated by $^3$H-Thymidine incorporation and β-radiation scintillation counting. Black bars represent $^3$H-Thymidine incorporation by PBLs co-cultivated with autologous DCs pulsed with inactivated HIV-1; white bars represent the $^3$H-Thymidine incorporation by control cultures.

Panel B shows the frequency of IFNγ-producing cells in cultures of PBLs stimulated with virus-pulsed DCs, as determined by enumeration of single IFNγ-producing cells by ELISPOT, using cells harvested at 24 hr after the $3^{rd}$ stimulation with virus-pulsed DCs. Each bar represents the mean spot number of triplicates ±S.D. per $10^6$ T cells. The number of HIV-reactive IFNγ-producing cells were calculated by subtraction of mean spot number of T cells induced by autologous unpulsed DCs from mean spot number of T cells induced by virus-pulsed DCs.

Panel C shows the levels of IFNγ and IL-4 production, assessed by ELISA of the supernatants of primary cultures stimulated as described above. Grey bars indicate cytokine concentration in the supernatant from PBLs co-cultured with virus-pulsed DCs, whereas white bars represent cytokine concentration in supernatant from control cultures.

Figure 10:
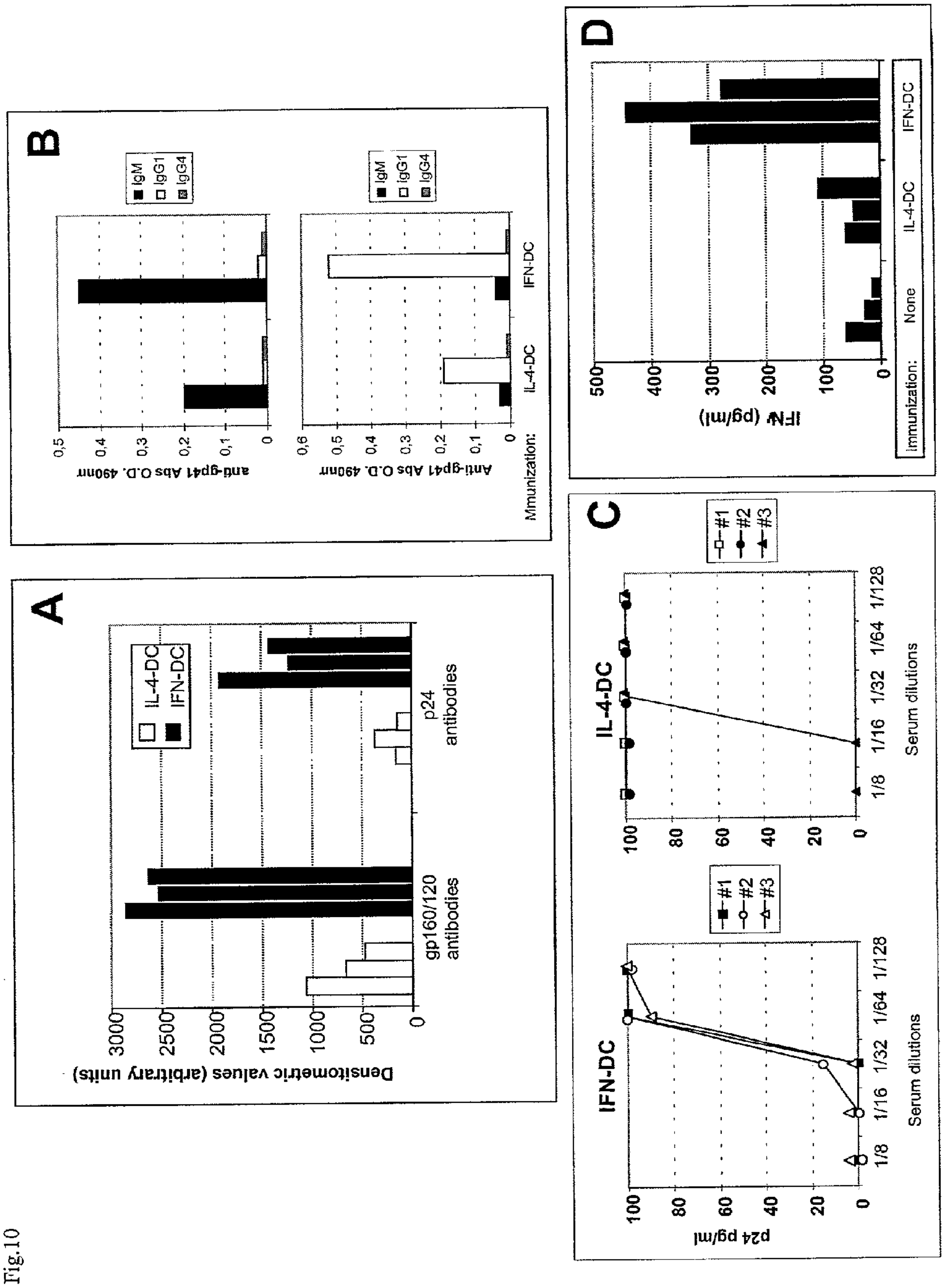

FIG. 10 depicts a representative experiment of “in vivo” induction of human primary response to HIV antigens in the hu-PBL-SCID mouse model (for experimental details, see examples). Panel A shows human anti-HIV-1 gp160/120 and p24 antibodies (total Ig) in the sera from individual hu-PBL-SCID mice immunized and boosted (7 days later) with $1.5\times10^6$ IFN-DCs or IL-4-DCs pulsed (2 hr at 37° C.) with AT-2 inactivated HIV-1 (IFN-DCs were obtained by treatment with IFNαn and GM-CSF for 3 days). Values were obtained by densitometric scanning of the corresponding bands after western blot assay. Panel B shows anti-gp41 antibody isotype characterization at days 7 and 14; bars represent the mean values obtained from three mice vaccinated with virus-pulsed IFN-DCs or IL-4-DCs. Panel C shows the “in vitro” neutralization activity against HIV of sera from immunized hu-PBL-SCID mice collected at day 21. Serial dilutions of sera from immunized hu-PBL-SCID mice were combined with 10 $TCID_{50}$ of HIV-1 SF162 strain and added to PHA activated PBMC. After 3 days, supernatants were assayed for p24 production. Plots represent neutralizing activity of sera from individual mice immunized with the different DCs. Panel C shows the level of human IFNγ production in the peritoneum of immunized and control hu-PBL-SCID mice, as evaluated by ELISA.

Figure 11:
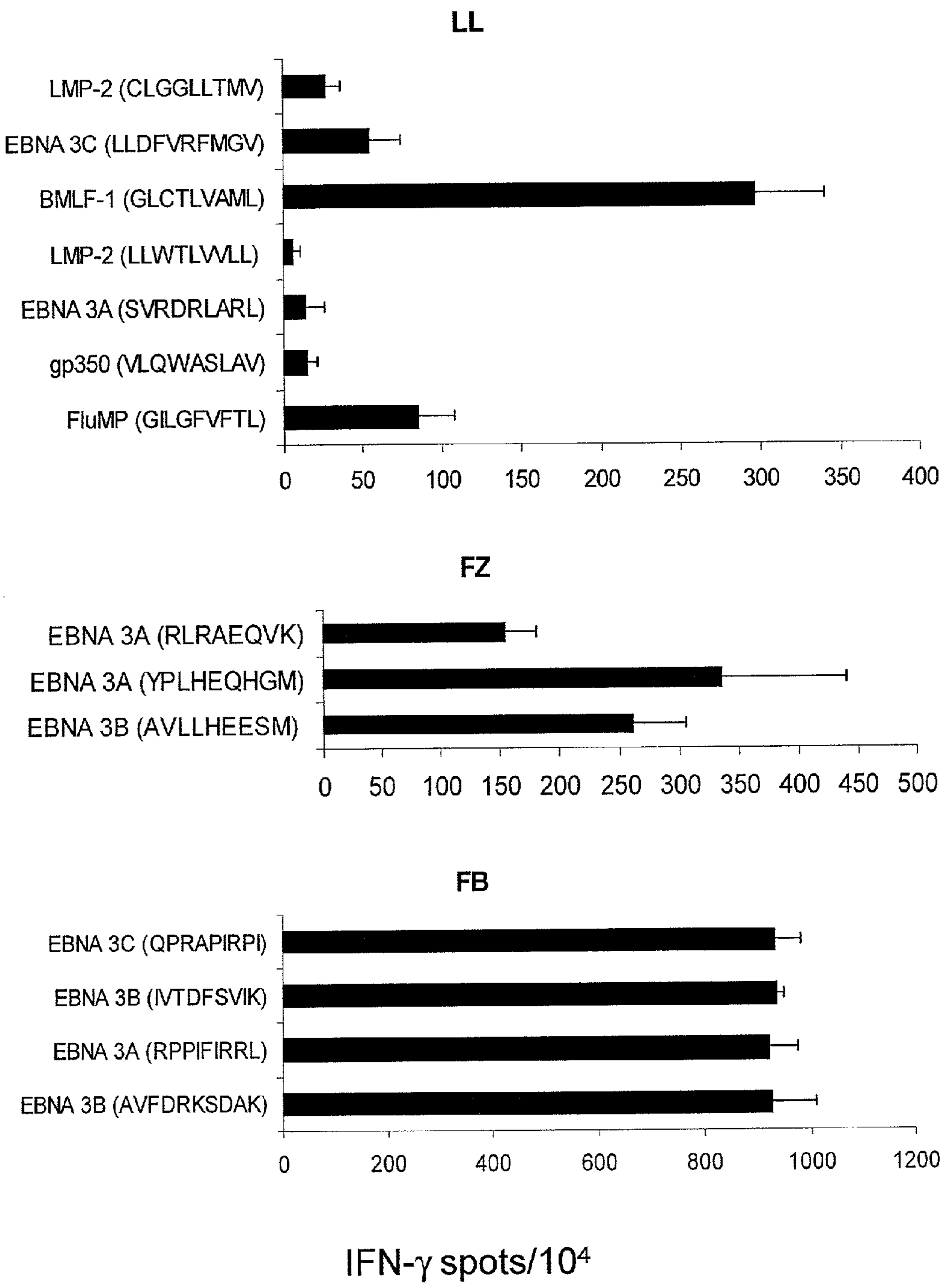

FIG. 11 illustrates the capacity of IFN-DCs pulsed with HLA class I-restricted peptides derived from different Epstein-Barr Virus (EBV) antigens to stimulate EBV-specific $CD8^+$ T cells after two rounds of stimulation. In order to evaluate the number of T cells producing IFN-γ, the ELISPOT assays were performed after an overnight incubation with autologous LCL (for donors FZ and FB) or peptide-pulsed T2 ($TAP^{-/-}$, HLA-A2) cells (for donor LL). Each bar represents the mean spot number of triplicates ±SD per $10^4$ T cells. The number of peptide-reactive cells per $10^4$ lymphocytes were calculated by subtraction of mean spot number of T cells induced by autologous unpulsed DCs from mean spot numbers of T cells induced by LCL (for donor FZ or FB) or peptide-pulsed T2 cells (for donor LL).

DETAILED DESCRIPTION OF THE INVENTION

Process for Deriving DCs in Vitro

Any mononuclear cell culture, such as purified or partially enriched CD14+ monocytes or PBMCs fractions, anyway obtained by a skilled person from human or animal tissues, can be treated according to the invention.

Blood-derived highly purified $CD14^+$ monocytes, adherent PBMCs or total PBMCs, which can be collected directly from patients without any prior pharmacological treatment to mobilize DC precursors, are however particularly suitable. For subsequent clinical use, cell collection is carried out by cytapheresis or by density gradient centrifugation of concentrated leukocyte apheresis. Cells are cultivated by standard equipments, flasks and incubators suitable for clinical use.

Total PBMCs, partially enriched or highly purified monocytes are then directly cultivated in the presence of type I IFN. Monocytes can be purified by depleting contaminating lymphoid cells using positive immunoselection by anti-CD14 microbeads (MACS Cell Isolation Kits, Miltenyi Biotec, Germany). Alternatively, microbeads conjugated to a monoclonal anti-hapten antibody directed to a cocktail of hapten-conjugated CD3, CD7, CD19, CD45RA and CD56 antibodies (MACS Cell Isolation Kits, Miltenyi Biotec, Germany) are used, as recommended by manufacturer.

Any other procedures or series of procedures ensuring production of a population of monocytes, can be used as well according to the invention.

In a particularly appropriated procedure, cells are processed and cultured in "closed processors" such as VACcell® processor (23), which include cell cultivation at 37° C. in 5% $CO_2$ humified air in gas-permeable hydrophobic bags (21), with medium and autologous serum in the presence of 1,000 IU/ml of type I IFN and 500 U/ml of GM-CSF. Serum-free media, human AB or autologous serum can be conveniently used as recognized by anyone skilled in the art to which the invention belongs.

Different types of standard media (e.g. RPMI-1630, MEM, Iscove's modified Dulbecco's Medium, Dulbecco's modified Eagle Medium) are used according to the subsequent use of DCs, whereas media suitable for treatment of human patients, such as X-VIVO 20 or AIM-V, are preferably used for culturing DCs to be employed in clinical protocols.

With regard to type I IFN suitable in the process of the invention, any type I IFN preparation can be used in the generation of IFN-DCs: recombinant IFNα: IFNα2b, IFNα2a, natural IFNα (IFNαn) from stimulated leukocytes from healthy subjects or natural lymphoblastoid IFNα, consensus IFN α (CIFN), and recombinant IFNβ. Relevant concentration shall be greater than 100 IU/ml even if ranges of 500-2,000 IU/ml, 500-1,000 IU/ml and particularly a concentration of 1,000 IU/ml are the most preferred. With regard to the up-regulation of costimulatory molecules, the optimal enhancing effects is observed with IFN doses ranging from 500 to 1,000 IU/ml, while 100 IU/ml of IFN does not result in any significant effect. Comparable enhancing effects on DC phenotype are obtained using different preparations of type I IFN such as natural IFN-α, IFNα2b, CIFN and IFNβ, which are added in conjunction with GM-CSF to blood-derived monocytes for 3 days of culture.

Accordingly, concentration adjustments could be necessary, following use of previously untested commercial preparations. A skilled person can in any case apply such an adjustment in function of the different IFN used and/or different culture condition used.

According to the invention, addition of IFN to the culture can be replaced by treatment with any substance capable of inducing type I IFN in culture, provided that the final concentration falls within the ranges above indicated.

Timing of the treatment is generally maintained within three days, at the end of which, non-adherent and loosely adherent DCs are collected.

Preferably, the cells recovered between day 2 and day 3 are used directly or purified by either elutriation in a counter current centrifuge or by immunomagnetic negative selection using beads conjugated to lineage specific antibodies. Alternatively, DCs can be conveniently cryopreserved for successive use.

In a particular embodiment of the invention, the process may include, following the derivation of DCs from mononuclear cells or from monocytes, a step of further maturation of the DCs, the maturation agent used being chosen among known maturation agents, such as a bacterial extract, poly-IC or CD40 ligand.

In a particular embodiment of the invention, the DCs obtained by the process described in the patent application may be loaded with antigenic peptides or proteins, or with a cellular extract containing at least one antigen. The cellular extract may consist of a cellular lysate or of apoptotic bodies prepared from the cells. Cells envisaged for this preparation may be lineage cells or autologous cells previously taken from the patient. Cells may be antigen loaded by pulsing with peptides, or by phagocytosis, pinocytosis, affinity binding, fusion, nucleic acid transfer or receptor mediated uptake, according to methods known by a man skilled in the art.

Type I IFNs used according to the above mentioned conditions were shown to induce a rapid differentiation of freshly isolated, preferably GM-CSF-treated human monocytes, into DCs endowed with potent functional activities both "in vitro" and "in vivo" in hu-PBL-SCID mice (24) and migration capability in response to chemotactic factors.

The comparison of DCs generated in the presence of IFN/GM-CSF with those obtained after IL-4/GM-CSF treatment revealed that type I IFN was definitively superior in inducing a rapid and stable differentiation process and in conferring a full capability to trigger a potent primary human immune response both "in vitro" and in hu-PBL-SCID mice.

DC Characterization: FACS Analysis, Cytokine Expression, Chemotactic Properties

A first indication of the different state of the two DC populations comes from FACS analysis revealing considerable differences in terms of membrane marker expression.

In this connection, three major types of phenotypic differences were in particular observed:

i. an early detachment of monocytes from culture plates in IFN-DCs, paralleled by rapid acquisition of high levels of CD40, CD54, CD80, CD86 and HLA-DR molecules within 3 days (FIG. 1), whereas IL-4/GM-CSF-treated monocytes required at least 6-7 days to fully acquire the immature DC phenotype;

ii. a selective expression of CD83 and CD25 (typical markers of mature DCs) in a considerable percentage of IFN-DCs (FIG. 1, Table 1); notably, in this connection CD83 expression was invariably associated with higher levels of HLA-DR and CD86; and iii. the significant expression of the membrane antigen CD123 (IL-3-receptor a-chain) (FIG. 1), which was much more expressed in IFN-DCs than in IL-4-DCs.

A further indication came from morphological analysis of the kind of DC population (FIG. 4), that revealed that IFN-DCs rapidly acquired typical DC features within 2-3 days, with the formation of markedly oriented dendrites, as clearly detected by immunocytochemistry after CD44 staining. The polarized CD44 staining of dendrites was further typical of IFN-DCs.

Notably, upon cytokine removal, IFN/GM-CSF-treated cultures retained the DC phenotype, without adhering to the flask surface, whereas IL-4/GM-CSF-treated DCs re-acquired the macrophage characteristics and readily re-adhered to culture flasks within three days, unless stimulated to terminally differentiate.

Figure 5:
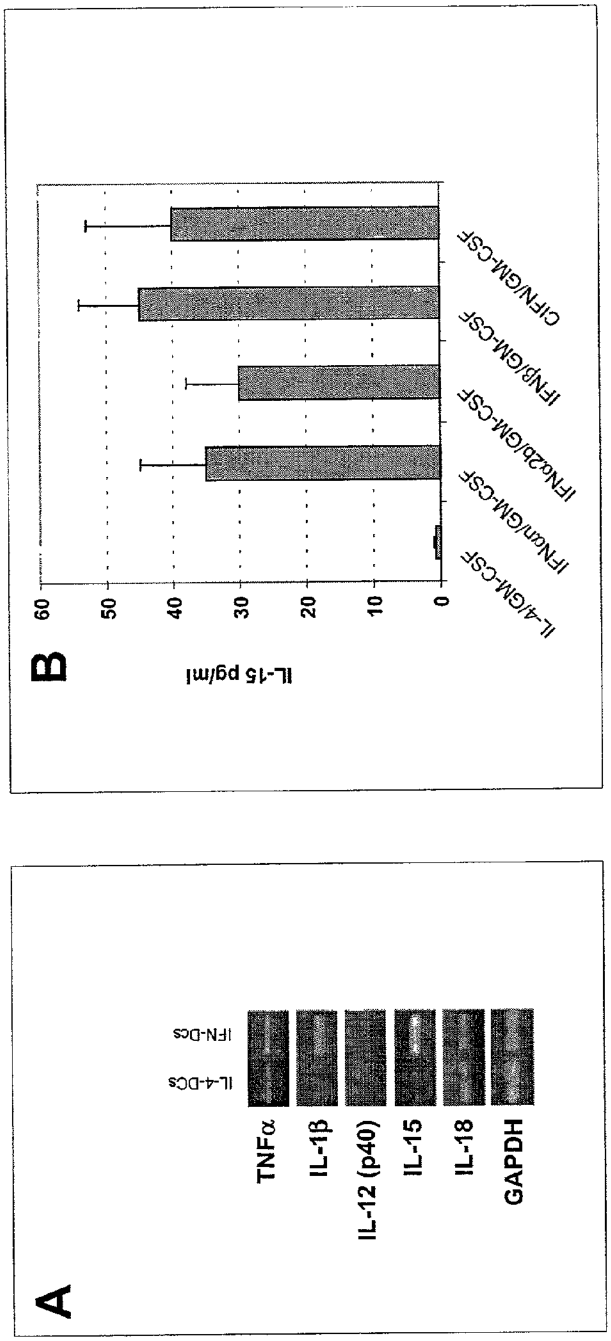
FIG. 5. Panel A shows RT-PCR analysis of cytokine mRNA expression in DCs generated in the presence of either type I IFN and GM-CSF or IL-4/GM-CSF for 3 days. RT-PCR was performed as described in the examples. Panel A shows photographs of PCR products, derived from specific amplification of different mRNAs, as evidenced by transillumination of 1.5% agarose electrophoresis gels stained with ethidium bromide.

A third indication of the mature/activated state of IFN-DCs vs. the immature state of IL-4-DCs came from the analysis of cytokine expression in the two DC populations, showing that IL-15 was expressed in IFN-DCs but not in IL4-DCs (FIG. 5).

A fourth indication came from the analysis of chemotactic properties. In fact, monocyte-derived IFN-DCs exhibited, with respect to IL-4-DCs, an enhanced expression of CCR5, which was associated with an enhanced migratory response to inflammatory β-chemokines (especially MIP-1β). Likewise, IFN-DCs expressed higher levels of CCR7 mRNA than IL-4-DCs along with an enhanced expression of CCR7 natural ligand, i.e. MIP-3β (FIG. 8A), consistent with the acquisition of a mature state. Notably, in this connection IFN-DCs showed potent migration response to MIP-3β, which was virtually absent in IL-4-DCs (FIG. 8B).

Of interest, the "in vitro" migration response to MIP-3β is associated with maturation, as evidenced by the CD83 upregulation in virtually all the migrated cells, further indicating that IFN-DCs had acquired an irreversible commitment towards maturation.

The evaluation of the chemokine expression (FIG. 8C) in IFN-DCs vs. IL-4-DCs revealed other major differences, which are consistent with a differential polarization of the immune response by the two DC populations. In particular, IFN-DCs expressed high levels of IP-10 and IL-15, while IL-4-DCs preferentially expressed MDC and TARC.

Functional Analysis

The method object of the invention presented herein is useful for the culture and rapid production of DCs to be used "in vitro" and "in vivo". The capacity of DCs to elicit potent antigen-specific immune helper and cytotoxic T cell response as well as humoral response allows to design and perform cellular therapy and immune intervention for any human or veterinary disease.

The production of large quantities of clinical grade DCs with type I IFN and GM-CSF allows their use as cellular vaccine adjuvant.

DCs generated in the presence of IFN/GM-CSF according to the process of the invention showed a potent ability to take up, process and present inactivated virus to autologous T lymphocytes "in vitro", which was clearly superior to that observed using DCs cultured with IL-4/GM-CSF (FIG. 9).

On the basis of these "in vitro" results, in particular the capability of HIV-1-pulsed DCs generated in the presence of either IFN/GM-CSF or IL-4/GM-CSF to elicit a primary human immune response "in vivo", has been evaluated by using SCID mice reconstituted with autologous PBL.

Remarkably, immunization of hu-PBL-SCID mice with autologous IFN-DCs pulsed with AT-2-inactivated HIV-1 resulted in the generation of a potent primary immune response towards HIV-1 antigens (FIG. 10A), as evaluated by the detection of specific human antibodies against the whole spectrum of viral proteins (not shown). At 7 days after immunization, human antibodies proved to be mostly IgM, while HIV-1-specific IgG1 antibodies were detected at 2 weeks, suggesting a Th1-like response (FIG. 10B).

Notably, the antibodies detected in the sera of mice injected with DCs generated in the presence of IFN had a potent neutralizing activity "in vitro" against HIV-1 (FIG. 10C).

The levels of human antibodies to HIV-1 were consistently higher in hu-PBL-SCID mice injected with DCs generated in the presence of type I IFN as compared to those detected in the xenochimeras immunized with the corresponding virus-pulsed DCs developed in the presence of IL-4.

In order to verify the ability of IFN-DCs to stimulate a $CD8^+$ T cell specific response, DCs were generated from monocytes of three different donors in the presence of GM-CSF/IFN and pulsed with single or pooled HLA class I-restricted peptides derived from different EBV antigens. Peptide-pulsed IFN DCs were then used to stimulate autologous PBLs. After two rounds of stimulation, the frequency of IFN-γ-producing T lymphocytes reactive against the majority of the selected peptides increased significantly in all the three donors, as assessed by ELISPOT assays (FIG. 11). In order to evaluate whether the EBV-specific $CD8^+$ T lymphocytes expanded after stimulation with peptide-pulsed IFN-DCs were capable of inhibiting lymphomagenesis in the hu-PBL-SCID chimeric model, SCID mice were reconstituted with PBMCs from one of the donors, previously tested for the ability of forming lymphomas after PBMCs injection into SCID mice. Vaccination of the reconstituted animals with autologous peptide-pulsed IFN-DCs caused a highly significant prolongation of survival time as compared to what observed for unvaccinated SCID mice and for mice vaccinated with unpulsed IFN-DCs (Table 2). Overall, these results indicate that IFN-DCs are efficient in stimulating the expansion of effector $CD8^+$ T lymphocytes.

As an alternative to the pulsing for 1-2 hours at 37° C. with peptides (in the range of 10-200 μg/ml), selected on the basis of the patient HLA haplotype and the type of response to be elicited, IFN-DCs can be pulsed with whole proteins or protein complexes.

In the case of malignancies exhibiting unknown tumor-associated antigens, IFN-DCs can be pulsed with tumor RNA complexed to cationic liposomes or with whole tumor cell lysates. Moreover, IFN-DCs can be induced to take up antigens by engulfing apoptotic or necrotic tumor cells or by exposure to cell lysates. In such cases, incubation time can be appropriately prolonged up to 4-5 hours. In fact, IFN-DCs were demonstrated to be able to phagocytose cell lysates, as well as fragments from apoptotic or necrotic tumor and virally infected cells "in vitro".

IFN-DCs can also efficiently internalize viral particles, bacteria and yeasts, permitting the targeting of multiple epitopes or complex antigens to DCs via inactivated or genetically-modified microorganisms. Moreover, even engineered DNA and RNA can be directly internalized, to deliver antigen-coding sequences to IFN-DCs.

In some cases, IFN-DCs do not need any pulse or tumor antigen administration before utilization, as in the case of IFN-DCs from chronic myelogenous leukemia (CML) patients, whose $CD14^+$ monocytes express the BCR-ABL fusion gene or other putative tumor antigens.

Possible routes of administration of antigen-loaded IFN-DCs are any route used for administering vaccine and include, whatever this antigen is, subcutaneous, intravenous, intraperitoneal, intramuscular, transdermal or intradermal injections, including intratumoral injection. An alternative modality of administration includes the slow i.v. infusion even with auxiliary external infusion pumps.

An additional modality of administering IFN-DCs can involve their direct injection within primary tumor or viral lesions, metastases or regional draining lymph node, even without prior incubation with specific antigens, which are locally acquired by IFN-DCs soon after injection. Administration modality and time schedule are designed and adjusted according to the age and weight of the patient, the disease and its severity as well as the response rate. Thus, $2\times10^6$ to $5\times10^7$ IFN-DCs can be infused once or at weekly/monthly time intervals according to the procedures described above.

IFN-DCs loaded with antigens can also be used for the "ex vivo" expansion of T cells, e.g. $CD4^+$ and/or $CD8^+$ or both, to be re-infused in patients. Such immune intervention can be useful in therapy of humans having immune disorders or deterioration, as in the course of persistent infections or neoplastic diseases.

EXAMPLES

Example 1

Derivation of DCs From Monocytes and Characterization of Immunophenotype and Morphology thereof Derivation of DCs From Monocytes Peripheral blood mononuclear cells were obtained from heparinized blood of normal donors by Ficoll density gradient centrifugation (Seromed). Monocytes were obtained either by 2 hr adhesion in 25-75 $cm^2$ flasks (Costar, Cambridge, Mass.) or by standard Percoll density gradient centrifugation.

Monocytes were further enriched by depleting contaminating cells using negative immunoselection by microbeads conjugated to a monoclonal anti-hapten antibody directed to a cocktail of hapten-conjugated CD3, CD7, CD19, CD45RA and CD56 antibodies (MACS Cell Isolation Kits, Miltenyi Biotec, Germany). After these procedures, the resulting cell population was represented by >95% $CD14^+$ monocytes, as assessed by flow cytometry.

Blood derived monocytes were plated at the concentration of 1-2×$10^6$ cells/ml in RPMI 1640 (Gibco BRL, Gaithesburg, Md.) supplemented with 10% FCS. GM-CSF (500 U/ml) was added in combination with the following cytokines: IL-4 (500 U/ml) (R & D Systems, Minneapolis, Minn.) and natural IFNα (1,000 IU/ml): IFNαn (Alfaferone Alfa-Wassermann).

All the IFN preparations used were shown to be free of any detectable LPS contamination. After 3 or 6 days of culture, non-adherent and loosely adherent cells were collected and used for subsequent analysis.

The experiments were carried out in order to compare type I IFN+GM-CSF treatment with IL-4+ GM-CSF treatment, currently used for obtaining immature DCs from monocytes in 6-7 days.

It has been observed in this connection that in response to IFN/GM-CSF treatment, adherent monocytes rapidly became floating non-adherent cells within 3 days. The loss of adherence was associated with cellular aggregation and large cell clusters were detected in the IFN/GM-CSF-treated cultures, while a large part of IL-4/GM-CSF-treated cells were still firmly adherent to the plastic surface. DCs so obtained have been therefore further characterized immunophenotipically and morphologically.

DC Immunophenotypical Characterization

Cells were washed and resuspended in PBS containing 1% human serum and incubated with a series of fluorochrome-conjugated mAbs to human antigens for 30 min at 4° C. The following mAbs were used for immunofluorescent staining: anti-CD14, -CD25, -CD54, -CD80 and -HLA-DR (Becton Dickinson, San Jose Calif.), -CD1a, -CD23, -CD40, -CD83 and -CD86 (Pharmingen, San Diego Calif.). Cells were analysed by flow cytometry. Data were collected and analysed by using a FACSort (Becton Dickinson) flow cytometer; data analysis was performed by CellQuest software (Becton Dickinson). DCs were electronically gated according to light scatter properties in order to exclude cell debris and contaminating lymphocytes.

Figure 1:
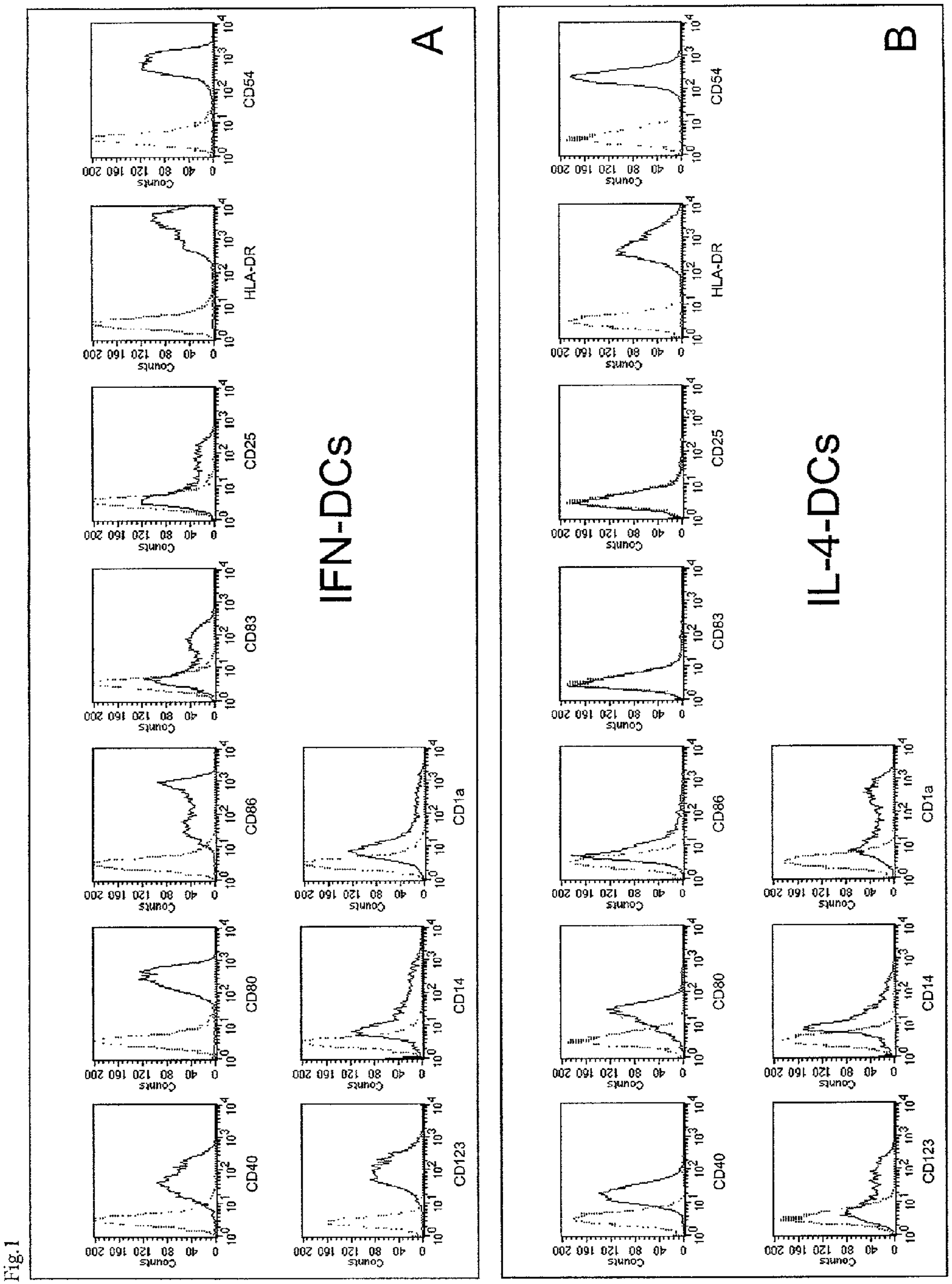
FIG. 1, shows the dot histogram analysis of the immunophenotype of DCs obtained by treating blood-derived $CD14^+$ monocytes for three days with 1,000 IU/ml of IFNαn (natural IFNα, Alfa-Wasserman) and 500 U/ml of GM-CSF (IFN-DCs) as compared to DCs obtained by treating monocytes with 500 U/ml of IL-4 and 500 U/ml of GM-CSF (IL-4-DCs) for three days. Monocytes were purified by standard Ficoll and 46% Percoll density gradient centrifugations followed by positive immunomagnetic sorting for $CD14^+$ cells (purity >95%). Monocytes were resuspended at the concentration of $2\times10^6$ cell/ml and treated as described in details in "Description of the invention" for 3 days. After staining with fluorochrome-conjugated monoclonal antibodies to cellular membrane markers, the cells were analyzed by flow cytometry, elettronically gating DCs according to light scatter properties, in order to exclude contaminating lymphocytes and cell debris. Data were acquired and analyzed using a FACSort flow cytometer and "Cell Quest" software (Becton Dickinson). The diagrams in the figure show the expression of a series of membrane markers in IFN-DCs (panel A) and IL-4-DCs (panel B). In each diagram, the x axis represents the cell fluorescence intensity relative to the analyzed marker, whereas the y axis represents the number of positive cells. Dotted lines represent the staining with isotype matched control antibodies to an irrelevant antigen.
Figure 2:
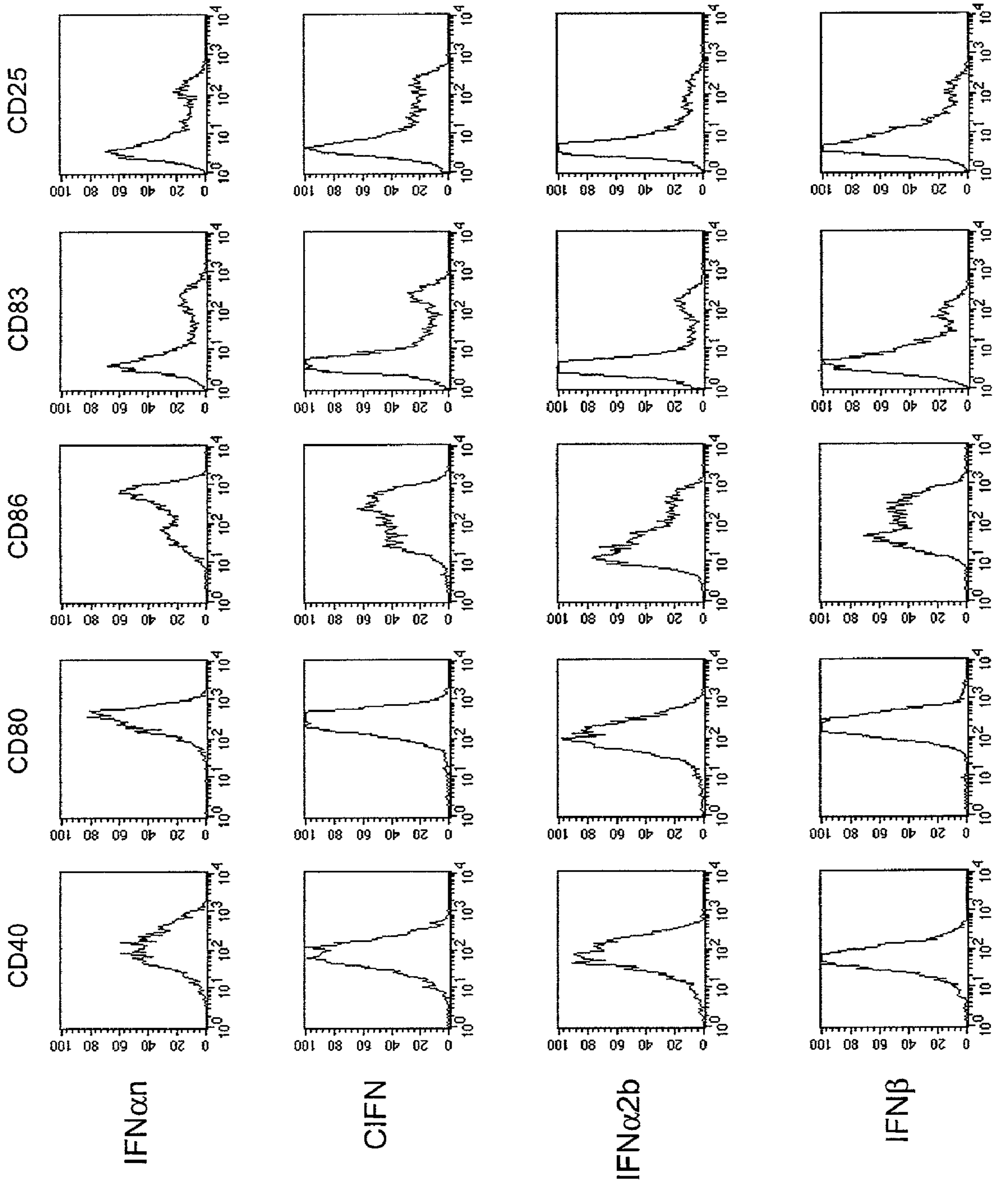
FIG. 2 shows comparative dot histogram profiles of DCs obtained from monocyte-enriched PBMCs treated with 1,000 IU/ml of different type I IFN preparations and 500 U/ml of GM-CSF, for three days. Monocyte fraction was enriched by standard Ficoll density gradient centrifugation and subsequent centrifugation on 46% Percoll density gradient of blood-derived PBMCs. After partial purification, the cell suspension contained <35% of contaminating lymphocytes. After staining with fluorochrome-conjugated monoclonal antibodies to surface markers, DCs were electronically gated according to light scatter properties and analyzed by flow cytometry as described in FIG. 1. In each diagram, showing the expression of specific surface markers, the x axis represents the cell fluorescence intensity, whereas the y axis represents the cell count. Control staining profiles were all within the first logaritmic decade of fluorescence intensity.

After 3 days of culture, cells treated with either IFN/GM-CSF or IL-4/GM-CSF were analyzed for the expression of surface markers associated with DC differentiation as well as of the monocytic marker CD14. Monocytes were purified by standard Ficoll and 46% Percoll density gradient centrifugations followed by immunomagnetic sorting. FIG. 1 illustrates the expression of selected markers upon treatment of monocytes with 1,000 IU/ml of IFNαn and 500 U/ml of GM-CSF (panel A) as compared to treatment with and 500 U/ml of IL-4 and 500 U/ml of GM-CSF (panel B). The up-regulation of costimulatory molecules (CD80, CD86 and CD40) was consistently higher in IFN-DCs than in IL-4-DCs as early as 3 days after cytokine treatment. Comparable enhancing effects on DC phenotype were observed using different type I IFNs (i.e., IFNαn, IFNα2b, CIFN and IFNβ) added in conjunction with GM-CSF to blood-derived monocytes for 3 days of culture. To this regard, FIG. 2 shows the comparison of the representative FACS profiles obtained at 3 days of cytokine treatment, wherein monocyte fraction was enriched by standard Ficoll density gradient centrifugation and subsequent centrifugation on 46% Percoll density gradient, and the different IFN preparations were used at the same concentration of 1,000 IU/ml.

Results of this comparison indicate that all type I IFN preparations are suitable for generating DCs.

In this connection, the following Table 1 summarizes the immunophenotypic features of DCs obtained from blood monocytes treated with 500 U/ml GM-CSF and 1,000 IU/ml of either IFNαn, IFNβ, or CIFN as compared to IL-4-DCs after three days of cytokine treatment. Freshly isolated monocytes were partially purified by Ficoll and Percoll density centrifugation and treated as described above. DCs were analyzed by flow cytometry, gating DCs according to light scatter properties. Data were acquired and analyzed by using a FACSort instrument and "Cell Quest" software (Becton Dickinson). Values represent the mean ±S.D. of nine experiments (three different experiments for each different type I IFN preparation). Values are obtained by dot histogram analysis of antigen expression and represent the mean percentage of positive cells for a given surface antigen and its Mean Fluorescence Intensity (MFI).

TABLE 1

Phenotype of IFN- and IL4-DCs after 3 days of cytokine treatment

| | IFN-DCs | | IL-4-DCs | |
|---|---|---|---|---|
| Marker | Percentage ± S.D. | MFI ± S.D. | Percentage ± S.D. | MFI ± S.D. |
| CD40 | 96 ± 11 | 87 ± 15 | 63 ± 11 | 26 ± 15 |
| CD80 | 91 ± 10 | 175 ± 83 | 70 ± 12 | 34 ± 7 |
| CD86 | 79 ± 20 | 254 ± 105 | 70 ± 7 | 81 ± 31 |
| CD83 | 25 ± 14 | 52 ± | 1 ± 3 | 43 ± |
| CD25 | 23 ± 12 | 50 ± 1 | 1 ± 0.5 | 33 ± 3 |
| HLA-DR | 96 ± 3 | 2060 ± 467 | 97 ± 2 | 1121 ± 263 |
| CD54 | 95 ± 4 | 641 ± 113 | 94 ± 3 | 239 ± 69 |
| CD14 | 36 ± 18 | 60 ± 1 | 13 ± 8 | 53 ± 15 |
| CD1a | 41 ± 17 | 105 ± 2 | 72 ± 17 | 284 ± 32 |

Notably, monocytes treated with IFN showed not only a marked up-regulation of costimulatory molecules and HLA-DR antigen, but also a clear-cut induction of the expression of the CD83 (15-40% of positive cells) and CD25 antigens, both considered as markers of mature/activated DCs. On the contrary, CD83 was expressed only by a strict minority of IL-4/GM-CSF-cultured DCs (1-4%).

The effects of different doses of type I IFN and in particular doses of 1,000 IU/ml, 500 IU/ml and 100 IU/ml have been therefore evaluated. Freshly isolated monocytes were isolated, cultured with cytokines and analyzed for antigen expression on day 3, to this purpose.

Figure 3:
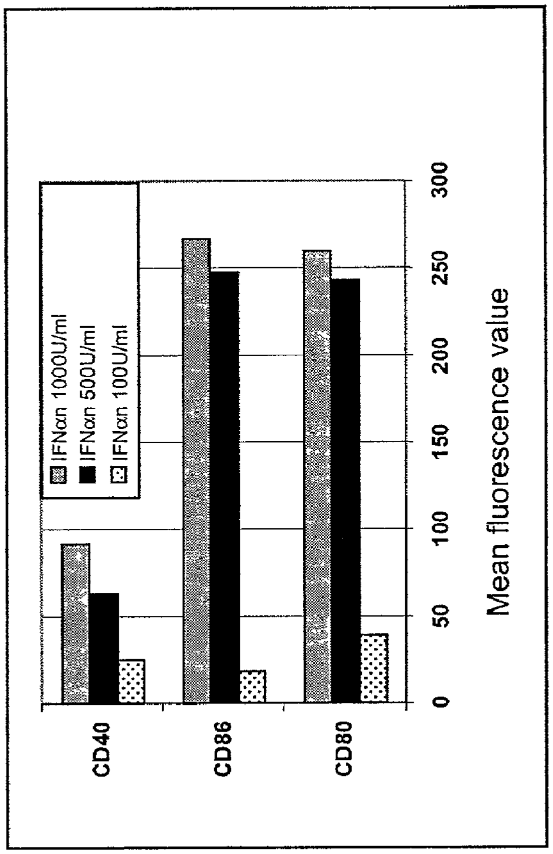
FIG. 3 shows a diagram comparing the effects of different doses of type I IFN, in particular 1,000 IU/ml, 500 IU/ml and 100 IU/ml, added together with 500 U/ml of GM-CSF, on the expression of costimulatory molecules. Freshly isolated monocytes were partially purified by Ficoll and Percoll density centrifugations, cultured with cytokines and analyzed for antigen expression on day 3, by flow cytometry. Representative data from one out of three experiments are shown. Bars represents the mean fluorescence intensity values of selected DC membrane antigens as indicated in the figure.

The relevant dose-response results shown in FIG. 3, indicated that the optimal type I IFN concentration for the upregulation of costimulatory molecules is within the range of 500-1,000 IU/ml, while 100 IU/ml of IFN did not result in any significant effect.

On the whole, these results underline that a 3-day exposure of freshly isolated monocytes to type I IFN/GM-CSF instead of IL-4/GM-CSF results in the generation of a characteristic type of partially mature DCs, as evidenced in particular by the significant expression of CD83 and CD25. These data show that IFN treatment not only induced an upregulation of costimulatory molecules, but also promoted the appearance of partially activated $CD83^+$ DCs.

The irreversible commitment of IFN-DCs to undergo an advanced maturation process was suggested by the finding that, upon cytokine removal, these cells retained a DC phenotype without adhering to the plastic surface, whereas IL-4-DCs re-acquired the macrophage features and readily re-adhered to culture plates within three days, unless preventively stimulated to terminally differentiate by LPS.

DC Morphological Characterization

In order to further detect potentially relevant differences between IFN-DCs and IL-4-DCs, immunocytochemical analysis was performed by using CD44 antibodies, since preliminary experiments had revealed that this protein was specifically expressed on dendrites and its staining clearly outlined these structures.

IFN- or IL4-DCs obtained after a 3 day-cytokine-treatment were spun onto glass slides (Shandon, Cheshire, UK) at the concentration of $10^4$ cells/ml, fixed with ethanol (70%) 10 min at +4° C. and stained by immunocytochemistry for CD44 (Dako, Denmark) using the peroxidase-anti-peroxidase (PAP/AEC) (Dako, Denmark) method. Cells were counter-stained with Mayer's haematoxilyn.

Figure 4:
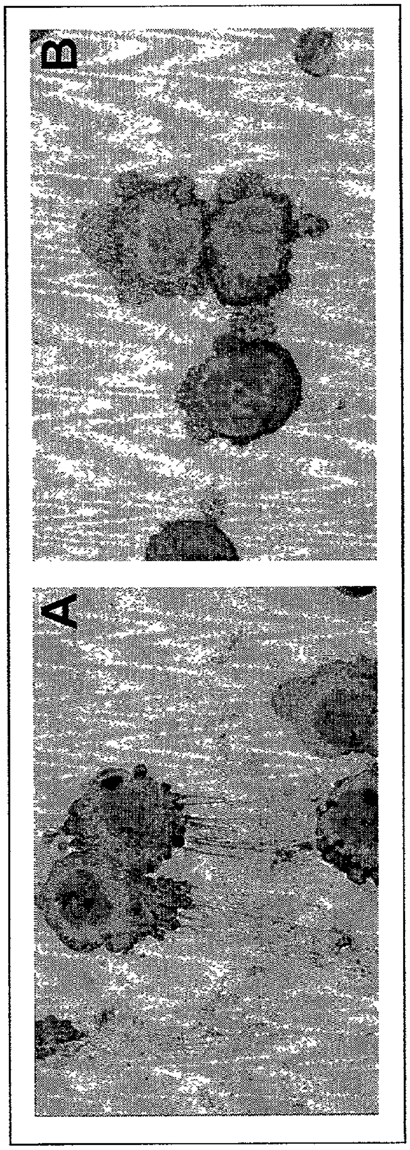
FIG. 4. Immunocytochemistry for CD44 expression in DCs generated in the presence of type I IFN (a) as compared to IL-4-DCs (b) (PAP/AEC and haematoxilyn counterstaining; magnification 1500×). The photos show the typical morphology of IFN/GM-CSF- and IL-4/GM-CSF-induced DCs. Note the thin and long dendrites of IFN-derived DCs as compared to the squat dendrites of the IL-4-DCs. Notably, the CD44 staining is typically localized on dendrites, nicely outlining them.

Clear-cut differences were observed in comparing IFN-DCs and IL-4-DCs at different culture times. In particular, a remarkable higher number of CD44 stained dendrites was observed in IFN-DCs as compared to IL-4-DCs (FIG. 4). The dendrites of IFN-DCs were mostly thin and long, reaching 21-30 μm of length (3-4 times the diameter of the cell body) and unidirectionally oriented (panel A). Notably, the CD44 staining is typically localized on dendrites nicely outlining them.

On the contrary, the typical $CD44^+$ stained morphology of IL-4-DCs (panel B) was that of larger cells with squat and short dendrites that highly resemble ruffles of different size.

In general, IL-4-DCs did not show the unidirectional orientation of dendrites typical of IFN-DCs. On the whole, these results were highly consistent with those obtained by Scanning Electron Microscopy and suggested that morphologic and phenotypic features characteristic of the blood DCs were generated after 2-3 days of treatment with type I IFN.

Example 2

Production of Cytokines by IFN-DCs and IL4-DCs

DCs produce a series of cytokines implicated in the initiation of the immune response especially when activated by mutual interaction with T cells or by encounter with viral pathogens and bacterial products. Thus, it was of interest to evaluate whether IFN/GM-CSF treated DCs exhibited any specific pattern of cytokine expression as compared to cells cultured in the presence of IL-4/GM-CSF. To this end a comparative RT-PCR analysis has been carried out.

Total RNA from DCs was extracted by RNAzol B and processed as previously described (24).

Transcripts were detected by amplifying the retro-transcribed RNA with specific primer pairs for:

```
IL-1       sense CTTCATCTTTGAAGAAGAACCTATCTTCTT,
           antisense AATTTTTGGGATCTACACTCTCCAGCT
           GTA),

TNFα       sense ATGAGCACTGAAAGCATGATCCGG,
           antisense GCAATGATCCCAAAGTAGACCTGCCC),

IL-12 p40  (sense CCAAGAACTTGCAGCTGAAGA,
           antisense TGGGTCTATTCCGTTGTGTC),

IL-15      (sense CTCGTCTAGAGCCAACTGGGTGAATGTAATAAG,
           antisense TACTTACTCGAGGAATCAATTGCAATCAAGA
           AGTG)
```

-continued

```
IL-18      (sense TCTGACTGTAGAGATAATGC,
           antisense GAACAGTGAACATTATAGATC);
```

GAPDH RT-PCR was run in parallel to normalize the levels of human RNA in all the samples. All RT-PCR products were in the linear range of amplification.

The relevant results, reported in FIG. 5A, showed that IFN-DCs expressed high levels of mRNA for IL-1β. Notably, induction of IL-15 expression was selectively detected in cultures treated with IFN/GM-CSF. As IL-15 expression is tightly regulated at the translational level, it was of interest to determine whether detectable levels of the cytokine could be revealed in the supernatants of IFN-treated cultures. Secretion of IL-15 in the supernatant of DCs differentiated in the presence of various type I IFN preparations and GM-CSF as compared to IL-4/GM-CSF treatment for 3 days is reported in FIG. 5B which shows that remarkable levels of IL-15 were secreted in response to the IFN/GM-CSF treatment.

Example 4

Allopeneic Stimulatory Capacity of IFN-DCs

Enhanced Allostimulatory Properties of DCs Generated in the Presence of IFN/GM-CSF.

A series of functional experiments has been carried out for comparing the ability of DCs generated from monocytes in the presence of IFN/GM-CSF or IL-4/GM-CSF to stimulate proliferation and IFNγ production by allogeneic PBLs in MLR assays.

Monocyte-depleted PBLs were seeded into 96 wells plates (Costar, Cambridge, Mass.) at $10^5$ cells/well. Purified allogeneic DCs ($5\times10^3$) were added to each well in triplicate. After 5 days, 1 μCi of methyl-$^3$H-Thymidine (Amersham) was added to each well and incubation was continued for additional 18 hr. Cells were finally collected by a Mach II Mcell (Tomtec) harvester and thymidine uptake was quantitated by liquid scintillation counting on 1205 Betaplate (Pharmacia).

As illustrated in FIG. 6A, wherein are reported the results of the comparative MLR assays in the presence of various preparations of type I IFN and GM-CSF or IL-4 /GM-CSF, IFN-DCs proved to be superior in inducing the proliferation of allogeneic PBLs as compared to IL-4-DCs, as revealed by $^3$H-thymidine incorporation assay.

Notably, DCs generated in the presence of 100 IU/ml IFN elicited a poor proliferative response, as showed in FIG. 6B, wherein the effects of the different concentrations of IFN in combination with 500 U/ml of GM-CSF on the ability of DCs to induce proliferation of allogeneic lymphocytes are reported.

This was not unexpected on the basis of the results reported above, since DCs generated with 100 IU/ml of IFN exhibited very low levels of co-stimulatory molecules, as determined by flow cytometric analysis (FIG. 3).

A specific feature of MLRs generated with IFN-DCs was the considerable IFNγ production, which was definitely higher than that found in the corresponding co-cultures using DCs generated with IL-4 (FIG. 6C), suggesting a prominent capability of IFN/GM-CSF-DCs to promote a Th1 response.

Example 5

Analysis of the Migratory Response to Chemokines

The migration and function of DCs is strictly regulated by their response to chemokines as well as by the expression of DC-derived chemokines, whose production can markedly shape DC functional activities. The attitude to migrate in response to chemotactic stimuli was analyzed in IFN-DCs and IL-4-DCS, together with the expression of chemokines/chemokine receptors in both DC populations.

a. Response to β-chemokines

Chemotactic response to inflammatory β-chemokines was studied by measuring the migration capability of DCs using a two compartment systems with chemokine containing medium (FIG. 7) Cell migration was performed in 24-well Transwell cell culture chambers (Costar). In brief, $5\times10^5$ cells cultured in complete medium with IFN/GM-CSF or IL4/GM-CSF for 3 days were resuspended in complete medium and seeded in the upper compartment of 8 μm-pore size filter Transwell chambers.

RANTES, MIP1α, MIP1β (500 ng/ml) (R&D System), were diluted in serum-free medium and added to the lower compartment, while the lower wells of control chamber contained medium alone. After 2 hr incubation at 37° C., the cells migrated through the 8 μm-pore size polycarbonate filters in the lower compartment were collected and counted. Each assay was performed in triplicate.

Of interest, the generation of DCs with type I IFN and GM-CSF in 3 days was associated with a stronger chemotactic response to the β-chemokine RANTES, MIP-1α and especially to MIP-1β, as compared to DCs generated with IL-4 and GM-CSF, suggesting an intrinsic attitude of IFN-DCs to promptly respond to inflammatory chemokines.

b. IFN-DCs Over-express CCR7 and Exhibit an Enhanced Capacity to Migrate in Response to Mip-3β.

Mature DCs have been reported to respond to MIP-3β/ELC and 6Ckine/SLC as a consequence of an up-regulation of their receptor (CCR7). Of interest, recent studies in knock-out mice for CCR7 have shown the crucial importance of the CCR7/MIP-3β interaction for the generation of a primary immune response (25). Thus, we evaluated the expression of CCR7 in IFN-DCs as compared to IL-4-DCs. Transcripts were detected by amplifying the retro-transcribed RNA with specific primer pairs for:

```
hCCR7     (sense TCCTTCTCATCAGCAAGCTGTC,
          antisense GAGGCAGCCCAGGTCCTTGAAG);

hMIP3β    (sense CACCCTCCATGGCCCTGCTACT
          antisense TAACTGCTGCGGCGCTTCATCT);
```

The samples were amplified for 25-35 cycles at the following conditions: 94° C. 40", 62° C. 40", 72° C. 40". To amplify hMIP-3β mRNA the annealing temperature was 58° C. α-actin RT-PCR was run in parallel to normalize the levels of human RNA in all the samples. All RT-PCR products were in the linear range of amplification. RT-PCR analysis revealed that IFN-DCs expressed higher levels of CCR7 mRNA as compared to IL-4-DCs, as shown in FIG. 8 (panel A), wherein the expression at mRNA level of the chemokine MIP-3β and its receptor CCR7 in IFN-DCs vs. IL-4-DCs is compared.

Of interest, when both types of DCs were tested for their capacity to migrate in response to the natural ligand of CCR7, a marked chemotactic response to MIP-3β was specifically observed for IFN-DCs. See in this connection panel B of FIG. 8 wherein the migratory response of IL-4-DCs vs. IFN-DCs (generated with GM-CSF and different type I IFN preparations as indicated), in response to Mip-3α and Mip-3β is compared. Thus, IFN-DCs were found to express CCR7 and to respond to its natural ligand Mip-3β very efficiently confirming that IFN-DCs, at least in part, exhibit features of mature DCs.

In another set of studies, mRNA from DCs was extracted by RNAzol B and processed as previously described to detect the expression of a set of chemokines. The following primer sets were used:

```
DC-CK1    (sense ACAAAGAGCTCTGCTGCCTC,
          antisense CCCACTTCTTATTGGGGTCA);

TARC      (sense CCTCCTCCTGGGGGCTTCTCTG,
          antisense GACTTTAATCTGGGCCCTTTGTGC);

IP-10     (sense TGATTTGCTGCCTTATCTTTCTGA -
          antisense CAGCCTCTGTGTGGTCCATCCTTG);

MDC       (sense CAGCCTGACAAATCACAGTG -
          antisense CTGGATGACACTGAGCTGG).
```

As shown in FIG. 8C, wherein RT-PCR analysis performed after 3 day treatment of monocytes with either IFN/GM-CSF or IL-4/GM-CSF is reported, the mRNA for DC-CK1, a chemokine specifically expressed by human DCs at high levels, was strongly expressed in IFN-DCs. Moreover, IP-10 mRNAs was expressed at higher levels in IFN-DCs with respect to IL-4-DCs, while MDC and TARC expression was up-regulated in IL-4-DCs.

Example 5

Primary Response to HIV Antigens Elicited by IFN-DCs "in vitro": Comparison with the Activity of DCs Generated in the Presence of IL-4/GM-CSF The ability of DCs generated in the presence of either IFN/GM-CSF or IL-4/GM-CSF to initiate a primary response in autologous PBLs was evaluated by using inactivated HIV-1 as an immunogen. To inactivate HIV, a recently described procedure (22) has been adopted, consisting in the use of 2,2'-dithiodipyridine (aldrithiol-2; AT-2), which inactivates HIV by selectively disrupting the p7 nucleocapsid (NC) protein, leaving intact the conformation and fusogenic activity of the gp120 HIV-1 protein (26).

Autologous PBLs were stimulated with DCs pulsed with AT-2-inactivated HIV-1. HIV-1 SF162 strain was inactivated by AT-2 and stored at −140° C. until use. PBLs ($4\times10^6$) were stimulated with $1\times10^6$ autologous DCs generated by treatment with either IFN/GM-CSF or IL-4/GM-CSF for 3 days and pulsed with AT-2-inactivated HIV-1 (40 ng of p24) for 2 hr at 37° C. Control cultures were incubated with unpulsed autologous DCs. PBLs were restimulated 7 days later with unpulsed or inactivated virus-pulsed DCs. Exogenous IL-2 (25 U/ml) was added every 4 days. At day 14, Proliferation assays were performed as follows: $5\times10^3$ unpulsed or inactivated virus-pulsed DCs were added to $10^5$ autologous PBLs into triplicate wells. After 6 days, 1 μCi of methyl-$^3$H-Thymidine was added to each well and incubation was continued for additional 18 hrs. Cells were collected and thymidine uptake was quantitated as described in Example 4.

Cells and supernatants from the cell cultures were also tested respectively for IFNγ production by ELISPOT analysis and ELISA.

Virus-pulsed IFN-DCs not only proved to be better stimulators of $^3$H-thymidine uptake by autologous PBLs than IL-4-

DCs, but also induced a stronger Th1-oriented response. In FIG. 9 (panel A) the results of lymphocyte proliferation assays to HIV antigens using DCs as APCs are reported. The frequency of IFNγ-producing cells (assessed by ELISPOT) and the levels of IL-4 and IFNγ production (measured by ELISA) in the primary cultures stimulated as described above are reported respectively on panel B and C of the same FIG. 9.

The evaluation of IFNγ-producing cells was performed by ELISPOT assay (Euroclone U.K.) according to the manufacturer's instructions. Briefly, 96-well plastic plates (Maxisorp Nunc) were coated with capture anti-IFNγ antibodies and blocked with 2% BSA. Ten-fold dilutions (from $10^5$ to $10^2$) of PBLs from primary cultures were restimulated overnight with DCs pulsed with inactivated HIV-1, added to triplicate wells and incubated for 18 hr. After cell removal, plates were incubated with an anti-IFNγ detection biotinylated antibody and streptavidin-conjugated alkaline phosphatase. Then, substrate solution was added and the frequency of IFNγ-producing cells was evaluated by enumerating single spots on an inverted microscope.

The ELISPOT analysis showed a higher number of IFNγ-producing cells in primary cultures stimulated with DCs generated with different preparations of type I IFN+GM-CSF as compared to cultures stimulated with IL-4-DCs, as shown in panel B of FIG. 9. These results were consistent with the secretion of higher levels of IFNγ in the supernatants of IFN-DCs, as shown in panel C of FIG. 9, wherein the levels of IL-4 and IFNγ production measured by ELISA in the supernatants of primary cultures stimulated as described above are reported. Notably, little or no secretion of IL-4 was detected in cultures stimulated with virus-pulsed IFN-DCs, while considerable amounts of this cytokine were found in the supernatants of cultures exposed to virus-pulsed IL-4-DCs (FIG. 9C).

Example 6

Primary Antibody Response to HIV Antigens Elicited by IFN-DCs in the hu-PBL-SCID Mouse Model: Comparison with the Activity of DCs Generated in the Presence of IL-4/GM-CSF The evaluation of the effects of IFN-DCs on the "in vivo" primary immunization and antibody response in the model of SCID mice reconstituted with human PBLs (27), was carried out. In fact, recent data have suggested that a human primary immune response can be generated in hu-PBL-SCID mice, especially when the chimeras are injected with antigen pulsed DCs (24, 28).

Four-week-old CB17 scid/scid female mice (Harlan, Nossan, Italy) were kept under specific pathogen-free conditions. SCID mice were housed in microisolator cages and all food, water and bedding were autoclaved prior to use. Hu-PBLs were obtained from the peripheral blood of healthy donors. All donors were screened for HIV-1 and hepatitis viruses prior to donation. The hu-PBLs were obtained by Ficoll-Paque density gradient centrifugation. Twenty million cells were resuspended in 0.5 ml of RPMI 1640 medium and injected i.p. into the recipient mice. Mice were injected i.p. with $2\times10^6$ autologous DCs, pulsed for 2 hr at 37° C. with AT-2 inactivated HIV-1 (100 ng of p24 per immunization dose). Seven days later, mice were given a boost dose of AT-2 inactivated HIV-pulsed DCs. At day 7 and 14, sera from hu-PBL-SCID mice were assayed for the presence of human anti-HIV antibodies.

The total spectrum of human antibodies against HIV-1 proteins was evaluated by performing Western Blot analysis with pooled sera from hu-PBL-SCID mice injected with virus-pulsed DCs. Sera from hu-PBL-SCID mice injected with HIV-1-pulsed DCs were assayed by Western blot (Cambridge Biotech HIV western blot Kit, Rockville Md.). Briefly, nitrocellulose strips were incubated overnight with individual mouse serum samples (diluted 1:20) or with a human positive control serum (diluted 1:1,000). Visualization of the human Igs specifically bound to HIV-1 proteins was obtained by incubation with substrate chromogen after the addition of biotin-conjugated goat anti-human IgG and streptavitin-conjugated horseradish peroxidase. Western blot strips were examined by densitometry using the Quantity One 4.2.1 software (Bio Rad) to detect the intensity of serum antibody reactivity towards the HIV-1 gp120/160 and p24 antigens. The mean values detected in the sera from 3 control non-immunized Hu-PBL-SCID mice were used as cut-off to determine the specific antibody reactivity in the serum from immunized chimeras.

An ELISA system was utilized to quantitate human total Igs, IgM, IgG1 and IgG4 immunoglobulins in the sera of the chimeras by using anti-human total Ig and anti IgM (Cappel-Cooper Biomedical, West Chester, Pa. and anti IgG1 or anti TgG4 (Pharmingen). All ELISAs were performed in duplicate and laboratory standards were included on each plate. Sera from non-reconstituted SCID mice were used as negative controls of all the ELISA determinations. ELISA for detection of specific anti-HIV antibodies was performed using a specific peptide (i.e., ERYLKDQQLLGIWGCS-GKLIC) corresponding to amino acids 591 to 611 of the HIV-1 gp41 protein. Synthetic peptides were immobilised on Dynatec (Dynal, Oslo, Sweden) microtitre plates by an overnight incubation at 4° C. Serially diluted mouse sera were added and incubated for 90 min at room temperature. Finally, binding was revealed by reading $A_{490}$ values after incubation with substrate chromogen. Values represent mean adsorbance value of each individual serum tested in duplicate. The cut-off value was calculated as mean adsorbance value of all the control sera plus 0.100 A. Sera showing $A_{490}$ values higher than this threshold were considered positive for anti-HIV antibodies.

Hu-PBL-SCID mice immunized with DCs generated in the presence of IFN/GM-CSF showed higher levels of anti-HIV antibodies directed to gp160/120 and p24 antigens, as compared to the xenochimeras injected with DCs obtained after IL-4/GM-CSF treatment. FIG. 10 (panel A) shows, in particular, the levels of human anti-HIV-1 gp160/120 and p24 antibodies (total Ig) detected in the sera from individual hu-PBL-SCID mice immunized and boosted (7 days later) with $1.5\times10^6$ IFN-DCs or IL-4-DCs, both pulsed (2 hr at 37° C.) with AT-2 inactivated HIV-1 (DCs were obtained by treatment with IFNαn and GM-CSF for 3 days). Values were obtained by densitometric scanning of the corresponding bands after western blot assay.

ELISA studies revealed the presence of high levels of anti-gp41 antibodies in hu-PBL-SCID mice immunized with HIV-1-pulsed IFN-DCs, as shown in panel B of FIG. 10, wherein anti-gp41 antibody isotype characterization at days 7 and 14, is reported. In this connection moreover, at day 7, anti-HIV-1 antibodies were shown to belong mainly to the IgM isotype (FIG. 10B) whereas, at day 14, antibodies belonging to the IgG1 isotype were detected especially in mice immunized with IFN/GM-CSF cultured DCs, revealing isotype switching upon antigen boost and suggesting a stronger Th1 biased response (FIG. 10B).

Remarkably, sera from hu-PBL-SCID mice immunized with virus-pulsed IFN-DCs were capable of recognizing virtually all the HIV-1 proteins detectable by Western blot analysis using a human positive control serum, as shown in panel C of FIG. 10, wherein the "in vitro" neutralization activity against HIV of sera from immunized hu-PBL-SCID mice collected at day 21 is reported.

Serial dilutions of sera from immunized hu-PBL-SCID mice were combined with 10 $TCID_{50}$ of HIV-1 SF162 strain and added to PHA activated PBMC. After 3 days, supernatants were assayed for p24 production. Notably, sera from xenochimeras immunized with IFN-DCs and exhibiting high levels of anti HIV-1 antibodies effectively neutralized HIV-1 infection of activated human PBL "in vitro".

Example 7

EBV Peptide-pulsed IFN-DCs as Stimulators of a $CD8^+$ T Cell Specific Response This example illustrates the capacity of IFN-DCs pulsed with HLA class I-restricted peptides derived from different EBV antigens to stimulate EBV-specific $CD8^+$ T cells. PBMCs were collected from three donors: LL (HLA-A2), FZ (HLA-A3, -B35), and FB (HLA-A11, -B27). After Ficoll-Percoll separation, the $CD14^+$ monocytes were purified by immunomagnetic method, used as fresh or cryopreserved samples, and the T cell-enriched fraction was cryopreserved in aliquots. DCs were generated by culturing monocytes at $2\times10^6$ cells/ml in the presence of GM-CSF/IFNαn (1,000 IU/ml) for 3 days and then pulsed with 10 μg/ml of EBV-derived peptides, known to be CTL epitopes presented by the HLA of the selected donors. Peptide-pulsed DCs were added to autologous T cell-enriched PBLs at different ratios. After 3-4 days, 10 U/ml of IL-2 were added to the cultures. T cells were restimulated with peptide-pulsed DCs, generated from cryopreserved monocytes, at 7 and 14 days after the initial co-culture. ELISPOT assays were performed after 7 days from each stimulation, in order to evaluate the number of T cells producing IFN-γ after an overnight incubation with autologous LCL (for donors FZ and FB) or peptide-pulsed T2 ($TAP^{-/-}$, HLA-A2) cells (for donor LL). Seven days after the first stimulation, the frequency of T lymphocytes specifically secreting IFN-γ varied with the peptides, but was in all cases lower than that observed after two stimulations (data not shown). FIG. 11 illustrates the results of the ELISPOT assays performed after two rounds of stimulation of T cells with autologous peptide-pulsed IFN-DCs. The number of peptide-reactive cells per $10^4$ lymphocytes were calculated by subtraction of mean spot number of T cells induced by autologous unpulsed DCs from mean spot numbers of T cells induced by LCL (for donor FZ or FB) or peptide-pulsed T2 cells (for donor LL). In particular, FIG. 11 illustrates the strong capacity of IFN-DCs pulsed with HLA class I-restricted peptides derived from different EBV antigens to stimulate EBV-specific $CD8^+$ T cells after two rounds of stimulation.

According to the results reported in FIG. 11 as for donor LL, a significant increase was observed in the frequency of T cells reactive against the BMLF-1-derived peptide, in particular, but also of T cells specific for the LMP-2 (CLGGLLTMV) and EBNA 3C (LLDFVRFMGV) peptides. As for donor FZ, a significant expansion of T cells specific for both the EBNA 3A-derived peptides as well as for the EBNA 3B-derived peptide was stimulated by peptide-pulsed IFN-DCs. As for donor FB, particularly high frequencies of IFN-γ-producing T cells reactive against the peptides derived from EBNA 3A, 3B, and 3C were obtained after two stimulations with peptide pulsed IFN-DCs. In order to evaluate the ability of IFN-DCs pulsed with EBV peptides to inhibit lymphomagenesis in SCID mice reconstituted with human PBMCs (hu-PBL-SCID) (29, 30), an in vivo experiment was performed. SCID mice were reconstituted with $4\times10^7$ PBMCs from donor FB (previously characterized for the ability of forming lymphomas into SCID mice), and received no treatment or two subsequent injections (3 hr after reconstitution and 7 days later) of unpulsed or peptide-pulsed IFN-DCs ($2\times10^6$ DCs/injection).

The DCs were generated from $CD14^+$ monocytes obtained from donor AB (the identical twin of donor FB) and cultured for 3 days with GM-CSF (500 U/ml) and IFNαn (1,000 IU/ml). The results, shown in the following Table 2, indicated that "vaccination" of the hu-PBL-SCID mice with peptide-pulsed IFN-DCs caused a highly significant prolongation of the survival time, as compared to untreated mice and to mice receiving unpulsed IFN-DCs.

TABLE 2

| Vaccine | Mean time of death (±SD) | | |
|---|---|---|---|
| None | 58.2 (±9.7) | NS | p< |
| Unpulsed IFN-DCs | 65.0 (±16.9) | p< | |
| Peptide-pulsed IFN-DCs | 90.6 (±2.3) | | |

Female CB17 scid/scid mice were reconstituted with $4\times10^7$ PBMCs from the EBV-positive donor FB. Three hours after reconstitution, the mice were divided into three groups.

The first group of mice received no further treatment, whereas mice in the second and third group were injected i.p. with, respectively, $2\times10^6$ unpulsed IFN-DCs or IFN-DCs pulsed with a pool of EBNA 3A, 3B, 3C peptides. These peptides were the same used for in vitro stimulations of donor FB PBL (see FIG. 11).

Seven days later, a boost dose ($2\times10^6$ cells) of unpulsed or peptide-pulsed IFN-DCs was injected i.p. in the second and third group of mice, respectively. The DCs utilized in this experiment were derived from $CD14^+$ monocytes obtained from donor AB, the identical twin of donor FB. There were five mice per group.

REFERENCES

1. Hart D N Dendritic cells: unique leukocyte populations which control the primary immune response. (1997) Blood 90:3245-87.
2. Banchereau J, Steinman RM Dendritic cells and the control of immunity. (1998) Nature 392:245-52
3. Bell D, Young J W, Banchereau J (1999) Dendritic cells Adv Immunol; 72:255-324.
4. Cella, M., F. Sallusto, and A. Lanzavecchia. Origin, maturation, and antigen-presenting function of dendritic cells. (1997) Curr. Opin. Immunol. 9: 10-16.
5. Jonuleit, H., K. Wiedemann, G. Muller, J. Degwert, U. Hoppe, J. Knop, and A. H. Enk. Induction of IL-15 messenger RNA and protein in human blood-derived dendritic cells: a role for IL-15 in attraction of T cells. (1997) J. Immunol. 158: 2610-2615.
6. Kuniyoshi, J. S., C. J. Kuniyoshi, A. M. Lim, F. Y. Wang, E. R. Bade, R. Lau, E. K. Thomas, and J. S. Weber. Dendritic cell secretion of IL-15 is induced by recombinant huCD40LT and augments the stimulation of antigen-specific cytolytic T cells. (1999) Cell. Immunol. 193: 48-58.

7. Vella A T, Dow S, Potter T A, Kappler J, Marrack P. Cytokine-induced survival of activated T cells in vitro and in vivo. (1998) Proc Natl Acad Sci U S A. 95:3810-5.
8. Borger, P., H. F. Kauffman, D. S. Postma, M. T. Esselink, and E. Vellenga. Interleukin-15 differentially enhances the expression of interferon-gamma and interleukin-4 in activated human (CD4+) T lymphocytes. (1999) Immunology 96: 207-214.
9. Avice, M. N., C. E. Demeure, G. Delespesse, M. Rubio, M. Armant, and M. Sarfati. IL-15 promotes IL-12 production by human monocytes via T cell-dependent contact and may contribute to IL-12-mediated IFN-gamma secretion by CD4+ T cells in the absence of TCR ligation. (1998). J. Immunol. 161: 3408-3415.
10. Sallusto F, Mackay C R, Lanzavecchia A The role of chemokine receptors in primary, effector, and memory immune responses. (2000) Annu Rev Immunol. 18:593-620
11. Dieu-Nosjean M. C., Vicari A., Lebecque S. and C. Caux. (1999) Regulation of dendritic cell trafficking: a process that involves the participation of selective chemokines. J. Leuk. Biol. 66:252-262.
12. Sozzani S., Allavena P., Vecchi A. and Mantovani A. Chemokines and dendritic cell traffic. (2000) J. Immunol. 20: 151-160.
13. Schall T. J. and K. B. Bacon. Chemokines, leukocyte trafficking and inflammation. (1994) Curr. Opin. Immunol. 6:865-873.
14. Sozzani S, Sallusto F, Luini W, Zhou D, Piemonti L, Allavena P, Van Damme J, Valitutti S, Lanzavecchia A, Mantovani A. Migration of dendritic cells in response to formyl peptides, C5a, and a distinct set of chemokines. (1995) J Immunol. 155:3292-5.
15. Sozzani S, Allavena P, D'Amico G, Luini W, Bianchi G, Kataura M, Imai T, Yoshie O, Bonecchi R, Mantovani A. Differential regulation of chemokine receptors during dendritic cell maturation: a model for their trafficking properties. (1998) J Immunol. 161:1083-6.
16. Quin S, Rottman J B, Myers P, Kassam N, Weinblatt M, Loetscher M, Koch A E, Moser B, Mackay C R The chemokine receptors CXCR3 and CCR5 mark subsets of T cells associated with certain inflammatory reactions. (1998) J Clin Invest. 101:746-754.
17. Liu M T, Chen B P, Oertel P, Buchmeier M J, Armstrong D, Hamilton T A, Lane T E The T cell chemoattractant IFN-inducible protein essential in host defense against viral-induced neurologic disease. (2000) J Immunol 165: 2327-2330
18. Andrew D P, Chang M, McNinch J, Wathen S T, Rihanek M, Tseng J, Spellberg J P, Elias III C G. STCP-1 (MDC) CC chemokine acts specifically on chronically activated Th2 lymphocytes and is produced by monocytes on stimulation with Th2 cytokine IL-4 and IL-13. (1998) J Immunol 161:5027-5038
19. Sallusto F, Lanzavecchia A. Efficient presentation of soluble antigen by cultured human dendritic cells is maintained by granulocyte/macrophage colony-stimulating factor plus interleukin 4 and downregulated by tumor necrosis factor alpha. (1994 ) J Exp Med. 179:1109-18.
20. Romani N, Gruner S, Brang D, Kampgen E, Lenz A, Trockenbacher B, Konwalinka G, Fritsch P O, Steinman R M, Schuler G. Proliferating dendritic cell progenitors in human blood. (1994) J Exp Med. 180:83-93.
21. Caux C, Dezutter-Dambuyant C, Schmitt D, Banchereau J. GM-CSF and TNF-alpha cooperate in the generation of dendritic Langerhans cells. (1992) Nature. 360:258-61.
22. Reddy A, Sapp M, Feldman M, Subklewe M, Bhardwaj N. A monocyte conditioned medium is more effective than defined cytokines in mediating the terminal maturation of human dendritic cells. (1997) Blood. 90:3640-6.
23. Goxe B, Latour N. Bartholeyns J, Romet-Lemonne J L, Chokri M. Monocyte-derived dendritic cells: development of a cellular processor for clinical applications. (1988) Res Immunol. 149:643-6.
24. Santini S. M., Lapenta C., Logozzi M. A., Parlato S., Spada M., Di Pucchio T. and Belardelli F. Type I Iinterferon as a powerful adjuvant for monocyte-derived dendritic cell development and activity in vitro and in Hu-PBL-scid mice. (2000) J. Exp. Med. 191: 1777-1788
25. Forster R, Schubel A, Breitfeld D, Kremmer E, Renner-Muller I, Wolf E, Lipp M. CCR7 coordinates the primary immune response by establishing functional microenvironments in secondary lymphoid organs. (1999) Cell. 99:23-33.
26. Rossio, J. L., M. T. Esser, K. Suryanarayana, D. K. Schneider, J. W. Jr. Bess, G. M. Vasquez, T. A. Wiltrout, E. Chertova, M. K. Grimes, Q. Sattentau, L. O. Arthur, L. E. Henderson, and J. D. Lifson. Inactivation of human immunodeficiency virus type 1 infectivity with preservation of conformational and functional integrity of virion surface proteins. (1998) J. Virol. 72: 7992-8001.
27. Mosier, D. E., R. J. Gulizia, S. M. Baird, and D. B. Wilson. Transfer of a functional human immune system to mice with severe combined immunodeficiency. (1988) Nature 335: 256-259.
28. Coccia, M. A., and P. Brams. High titer, prostate specific antigen-specific human IgG production by hu-PBL-SCID mice immunized with antigen-mouse IgG2a complex-pulsed autologous dendritic cells. (1998) J. Immunol. 161: 5772-5780.
29. Mosier D E, Gulizia R J, Baird S M, Spector S, Spector D, Kipps T J, Fox R I, Carson D A, Cooper N, Richman D D, et al. Studies of HIV infection and the development of Epstein-Barr virus-related B cell lymphomas following transfer of human lymphocytes to mice with severe combined immunodeficiency. (1989) Curr Top Microbiol Immunol. 152:195-9.
30. Rowe M, Young L S, Crocker J, Stokes H, Henderson S, Rickinson A B. Epstein-Barr virus (EBV)-associated lymphoproliferative disease in the SCID mouse model: implications for the pathogenesis of EBV-positive lymphomas in man. (1991) J Exp Med. 173:147-58.

The invention claimed is:

1. A process for deriving dendritic cells from mononuclear cells in culture wherein said mononuclear cells are peripheral blood mononuclear cells (PBMC) or CD14+ monocytes, comprising culturing said mononuclear cells for a maximum of three days with type I interferon (IFN) at a concentration of 400 to 10,000 IU/ml in the presence of GM-CSF at a range of 250-1,000 IU/ml, and in the absence of IL-4, and recovering dendritic cells from said culture.

2. The process according to claim 1, wherein said type I IFN is selected from the group consisting of natural IFN-alpha, recombinant species of IFN-alpha, natural IFN-beta, recombinant IFN-beta and consensus IFN $\alpha$ (CIFN).

3. The process according to claim 1, wherein type I IFN is present in the culture medium at a concentration in a range of 500-10,000 IU/ml.

4. The process according to claim 3, wherein type I IFN is present in the culture medium at a concentration of 1,000 IU/ml.

5. The process according to claim 1, wherein said GM-CSF is at a concentration in a range of 500-1,000 IU/ml.

6. The process according to claim 1, further comprises contacting dendritic cells, obtained by treating mononuclear cells with type I-IFN, with a maturation agent selected from the group consisting of bacterial extract, poly-IC and CD40 ligand.

7. A method for the ex vivo derivation of dendritic cells from mononuclear cells within 3 days of culture, wherein said mononuclear cells are peripheral blood mononuclear cells (PBMC) or CD14+ monocytes, comprising culturing type I IFN for a maximum of 3 days with said mononuclear cells from the beginning of said culture at a concentration range of 500 to 10,000 IU/ml, in the presence of GM-CSF at a concentration in a range of 500-1,000 IU/ml, and in the absence of IL-4.

8. The method according to claim 7, wherein said type IFN concentration is in a range of 500-2,000 IU/ml.

9. The method according to claim 8, wherein said type I IFN concentration is 1,000 IU/ml.

10. A method for the ex vivo derivation of dendritic cells from mononuclear cells, wherein said mononuclear cells are isolated peripheral blood mononuclear cells (PBMC) or isolated CD14+ monocytes, comprising culturing said isolated peripheral blood mononuclear cells (PBMC) or isolated CD14+ monocytes for a maximum of 3 days in a culture with type I IFN at a concentration 400-10,000 IU/ml and GM-CSF in a concentration of 250-1,000 IU/ml and in the absence of added IL-4, and collecting said cells within 3 days of culture.

11. The method according to claim 10, wherein said type I IFN concentration is in a range of 500-10,000 IU/ml.

12. The method according to claim 11, wherein said type I IFN concentration is in a range of 500-1,000 IU/ml.

13. A process for producing dendritic cells from mononuclear cells wherein said mononuclear cells are peripheral blood mononuclear cells (PBMC) or CD14+ monocytes, comprising culturing said mononuclear cells for a maximum of 3 days with type I interferon (IFN) at a concentration in the range of 400-10,000 IU/ml in the presence of GM-CSF at a concentration in a range of 250-1,000 IU/ml, and wherein said dendritic cells express higher levels of CD83 and CD25 antigens as compared to mononuclear cells or monocytes that have been cultured within 3 days of treatment with GM-CSF and IL-4.

14. The process according to claim 13, wherein levels of CD40, CD54, CD80, CD86 and HLA-DR molecules are in higher levels as compared to mononuclear cells of monocytes treated with IL-4 and GM-CSF within 3 days of culture.

15. The process according to claim 13, wherein said dendritic cells express high levels of IP-10 and IL-15 as compared to mononuclear cells or monocytes within 3 days of culture that are treated with IL-4 and GM-CSF.

16. The process according to claim 13, wherein an early detachment monocytes from the culture plates occurs during said process, and said dendritic cells exhibit high levels of CD40, CD54, CD80, CD86 and HLA-DR molecules as compared to mononuclear cells or monocytes within 3 days of culture with IL-4 and GM-CSF; wherein said dendritic cells express higher levels of CD83 and CD25 as compared to mononuclear cells or monocytes within 3 days of culture with IL-4 and GM-CSF; and wherein CD123 is more expressed in said dendritic cells as compared to mononuclear cells or monocytes that have been treated for 3 days with GM-CSF and IL-4.

17. The process according to claim 13, wherein said dendritic cells express higher levels of HLA-DR as compared to mononuclear cells or monocytes that have been cultured within 3 days of treatment with GM-CSF and IL-4.

18. The process according to claim 13, wherein said dendritic cells retain a dendritic cell phenotype without adhering to a plastic surface, whereas monocyte cells or monocytes treated with IL-4 and GM-CSF for 3 days re-aquire macrophage characteristics and re-adhere to culture flasks, unless stimulated to terminally differentiate.

19. The process according to claim 14, wherein said mononuclear cells or monocytes cultured with IL-4 and GM-CSF are cultured with 500 U/ml of CM-CSF and 500 U/ml of IL-4.

20. The process according to claim 15, wherein said mononuclear cells or monocytes cultured with IL-4 and GM-CSF are cultured with 500 U/ml of GM-CSF and 500 U/ml of IL-4.

21. The process according to claim 16, wherein said mononuclear cells or monocytes cultured with IL-4 and GM-CSF are cultured with 500 U/ml of GM-CSF and 500 U/ml of IL-4.

22. The process according to claim 17, wherein said mononuclear cells or monocytes cultured with IL-4 and GM-CSF are cultured with 500 U/ml of GM-CSF and 500 U/ml of IL-4.

* * * * *